(12) United States Patent
Lu et al.

(10) Patent No.: US 11,247,041 B2
(45) Date of Patent: Feb. 15, 2022

(54) WEARABLE CARDIOVERTER DEFIBRILLATOR (WCD) WITH ECG PREAMP HAVING ACTIVE INPUT CAPACITANCE BALANCING

(71) Applicant: West Affum Holdings Corp., Grand Cayman (KY)

(72) Inventors: Zhong Qun Lu, Everett, WA (US); Douglas K. Medema, Everett, WA (US); Kenneth F. Cowan, Kirkland, WA (US)

(73) Assignee: West Affum Holdings Corp., Grand Cayman (KY)

( * ) Notice: Subject to any disclaimer, the term of this patent is extended or adjusted under 35 U.S.C. 154(b) by 96 days.

(21) Appl. No.: 16/538,135

(22) Filed: Aug. 12, 2019

(65) Prior Publication Data

US 2020/0046962 A1 Feb. 13, 2020

Related U.S. Application Data

(60) Provisional application No. 62/717,538, filed on Aug. 10, 2018.

(51) Int. Cl.
*A61N 1/04* (2006.01)
*A61N 1/39* (2006.01)
(Continued)

(52) U.S. Cl.
CPC ............ *A61N 1/046* (2013.01); *A61B 5/0205* (2013.01); *A61B 5/316* (2021.01); *A61B 5/361* (2021.01);
(Continued)

(58) Field of Classification Search
CPC .... A61N 1/046; A61N 1/3904; A61N 1/3993; A61N 1/3925; A61N 1/0484;
(Continued)

(56) References Cited

U.S. PATENT DOCUMENTS 3,724,355 A 4/1973 Unger
3,724,455 A 4/1973 Unger
(Continued)

FOREIGN PATENT DOCUMENTS

WO 98/39061 A2 9/1998

OTHER PUBLICATIONS

Pagan-Carlo, et al., "Enciicling Overlapping Multipulse Shock Waveforms for Transthoracic Defibrillation," JACC Journals, Dec. 1998, vol. 32 Issue 7, p. 2065-2071.
(Continued)

*Primary Examiner* — Amanda K Hulbert
*Assistant Examiner* — Natasha Patel
(74) *Attorney, Agent, or Firm* — Spectrum IP Law Group LLC

(57) ABSTRACT

A wearable cardioverter defibrillator (WCD) comprises a plurality of electrocardiography (ECG) electrodes, a right-leg drive (RLD) electrode, and a plurality of defibrillator electrodes to contact the patient's skin when the WCD is delivering therapy to the patient, a preamplifier coupled to the ECG electrodes and the RLD electrode to obtain ECG data from the patient as one or more ECG vectors, a high voltage subsystem to provide a defibrillation voltage to the patient through the plurality of defibrillator electrodes, and an impedance measurement circuit to measure an impedance across a first pair of ECG electrodes, wherein the impedance measurement circuit is to apply a balancing impedance across a second pair of ECG electrodes when an impedance of the second pair of ECG electrodes is not being measured.

15 Claims, 15 Drawing Sheets

(51) Int. Cl.
*A61B 5/00* (2006.01)
*A61B 5/0205* (2006.01)
*A61B 5/316* (2021.01)
*A61B 5/361* (2021.01)

(52) U.S. Cl.
CPC .......... *A61B 5/6823* (2013.01); *A61N 1/0484* (2013.01); *A61N 1/3904* (2017.08); *A61N 1/3925* (2013.01); *A61N 1/3993* (2013.01)

(58) Field of Classification Search
CPC ........ A61N 1/025; A61B 5/316; A61B 5/361; A61B 5/6823; A61B 5/0205; A61B 5/282; A61B 5/6805
See application file for complete search history.

(56) References Cited

U.S. PATENT DOCUMENTS

| | | | |
|---|---|---|---|
| 4,583,524 | A | 4/1986 | Hutchins et al. |
| 4,619,265 | A | 10/1986 | Morgan et al. |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Bornn et al. |
| 5,353,793 | A | 10/1994 | Bornn |
| RE34,800 | E | 11/1994 | Hutchins |
| 5,394,892 | A | 3/1995 | Kenny |
| 5,405,362 | A | 4/1995 | Kramer et al. |
| 5,474,574 | A | 12/1995 | Payne et al. |
| 5,662,690 | A | 9/1997 | Cole et al. |
| 5,782,878 | A | 7/1998 | Morgan et al. |
| 5,792,204 | A | 8/1998 | Snell |
| 5,902,249 | A | 5/1999 | Lyster |
| 5,913,685 | A | 6/1999 | Hutchins |
| 5,944,669 | A | 8/1999 | Kaib |
| 6,047,203 | A | 4/2000 | Sackner et al. |
| 6,065,154 | A | 5/2000 | Hulings et al. |
| 6,108,197 | A | 8/2000 | Janik |
| 6,148,233 | A | 11/2000 | Owen et al. |
| 6,201,992 | B1 | 3/2001 | Freeman |
| 6,263,238 | B1 | 7/2001 | Brewer et al. |
| 6,287,328 | B1 | 9/2001 | Snyder et al. |
| 6,304,780 | B1 | 10/2001 | Owen et al. |
| 6,319,011 | B1 | 11/2001 | Motti et al. |
| 6,334,070 | B1 | 12/2001 | Nova et al. |
| 6,356,785 | B1 | 3/2002 | Snyder |
| 6,427,083 | B1 | 7/2002 | Owen et al. |
| 6,437,083 | B1 | 7/2002 | Owen et al. |
| 6,529,875 | B1 | 3/2003 | Nakajima |
| 6,546,285 | B1 | 4/2003 | Owen et al. |
| 6,671,545 | B2 | 12/2003 | Fincke |
| 6,681,003 | B2 | 1/2004 | Linder et al. |
| 6,762,917 | B1 | 7/2004 | Verbiest et al. |
| 7,065,401 | B2 | 6/2006 | Worden |
| 7,559,902 | B2 | 7/2009 | Ting et al. |
| 7,865,238 | B2 | 1/2011 | Brink |
| 7,870,761 | B2 | 1/2011 | Valentine et al. |
| 7,974,689 | B2 | 7/2011 | Volpe et al. |
| 8,135,462 | B2 | 3/2012 | Owen et al. |
| 8,140,154 | B2 | 3/2012 | Donnelly et al. |
| 8,369,944 | B2 | 2/2013 | Macho et al. |
| 8,548,557 | B2 | 10/2013 | Garstka et al. |
| 8,615,295 | B2 | 12/2013 | Savage et al. |
| 8,644,925 | B2 | 2/2014 | Volpe et al. |
| 8,897,860 | B2 | 11/2014 | Volpe et al. |
| 8,904,214 | B2 | 12/2014 | Volpe et al. |
| 8,965,500 | B2 | 2/2015 | Macho et al. |
| 9,008,801 | B2 | 4/2015 | Kaib et al. |
| 9,089,685 | B2 | 7/2015 | Sullivan et al. |
| 9,131,901 | B2 | 9/2015 | Volpe et al. |
| 9,132,267 | B2 | 9/2015 | Kaib |
| 9,408,548 | B2 | 8/2016 | Volpe et al. |
| 9,454,219 | B2 | 9/2016 | Volpe et al. |
| 9,592,403 | B2 | 3/2017 | Sullivan |
| 10,322,291 | B2 | 6/2019 | Medema et al. |
| 2003/0158593 | A1 | 8/2003 | Heilman et al. |
| 2005/0107833 | A1 | 5/2005 | Freeman et al. |
| 2005/0107834 | A1 | 5/2005 | Freeman et al. |
| 2006/0178706 | A1* | 8/2006 | Lisogurski ........... A61N 1/0492 607/10 |
| 2008/0312709 | A1 | 12/2008 | Volpe et al. |
| 2009/0005827 | A1 | 1/2009 | Weintraub et al. |
| 2010/0007413 | A1 | 1/2010 | Herleikson |
| 2010/0298899 | A1 | 11/2010 | Donnelly et al. |
| 2011/0022105 | A9 | 1/2011 | Owen et al. |
| 2011/0288604 | A1 | 11/2011 | Kaib et al. |
| 2011/0288605 | A1 | 11/2011 | Kaib et al. |
| 2012/0112903 | A1 | 5/2012 | Kaib et al. |
| 2012/0144551 | A1 | 6/2012 | Guldalian |
| 2012/0150008 | A1 | 6/2012 | Kaib et al. |
| 2012/0158075 | A1 | 6/2012 | Kaib et al. |
| 2012/0265265 | A1 | 10/2012 | Razavi et al. |
| 2012/0283794 | A1 | 11/2012 | Kaib et al. |
| 2012/0293323 | A1 | 11/2012 | Kaib et al. |
| 2012/0302860 | A1 | 11/2012 | Volpe et al. |
| 2012/0310315 | A1 | 12/2012 | Savage et al. |
| 2013/0085538 | A1 | 4/2013 | Volpe et al. |
| 2013/0231711 | A1 | 9/2013 | Kaib et al. |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |
| 2013/0325078 | A1 | 12/2013 | Whiting et al. |
| 2014/0025131 | A1 | 1/2014 | Sullivan et al. |
| 2014/0070957 | A1 | 3/2014 | Longinotti-Buitoni et al. |
| 2014/0163663 | A1 | 6/2014 | Poddar et al. |
| 2014/0324112 | A1 | 10/2014 | Macho et al. |
| 2014/0378812 | A1 | 12/2014 | Saroka et al. |
| 2015/0039053 | A1 | 2/2015 | Kaib et al. |
| 2015/0328472 | A1 | 11/2015 | Sullivan et al. |
| 2016/0004831 | A1 | 1/2016 | Carlson et al. |
| 2016/0082277 | A1 | 3/2016 | Foshee, Jr. et al. |
| 2016/0361533 | A1* | 12/2016 | Savage ................ A61N 1/0472 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev Fl, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

* cited by examiner

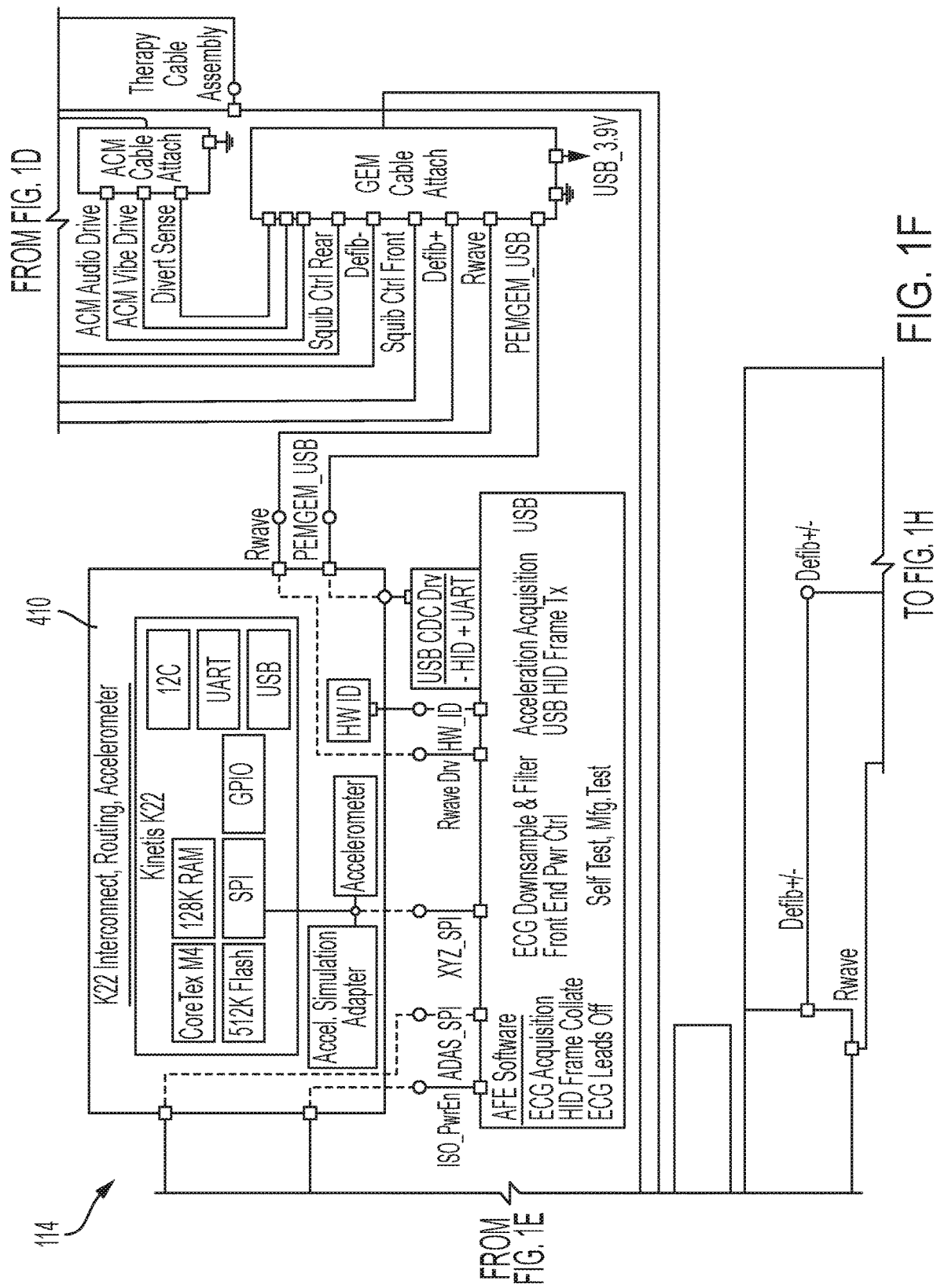

WEARABLE CARDIOVERTER DEFIBRILLATOR (WCD) WITH ECG PREAMP HAVING ACTIVE INPUT CAPACITANCE BALANCING

CROSS-REFERENCE TO RELATED APPLICATIONS

The present application claims the benefit of U.S. Provisional Application No. 62/717,538 filed Aug. 10, 2018. Said Application No. 62/717,538 is hereby incorporated herein by reference in its entirety.

BACKGROUND

The present art in electrocardiogram (ECG) preamps typically involves an electronic circuit with a fixed topology. In some cases, a variable number of electrodes can be selected to be monitored or a different reference electrode can be selected, for example the Right Arm (RA) electrode can be the reference rather than the more common Wilson Central Terminal of Right and Left Arms (LA) and Left Leg (LL) using the formula (RA+LA+LL)/3. Some ECG preamps also can support impedance measurement such as for measuring the patient's respiration, typically through a fixed pair of electrodes, for example the RA and LA electrodes. Generally, these changes in topology do not result in significant changes to the capacitive loading on any given ECG electrode and thus do not have a significant effect on the common mode rejection ratio (CMRR) of the preamp.

There are situations, however, where it may be advantageous to be able to switch which pair of electrodes is being used for impedance measurement, for example when using a Wearable Cardioverter Defibrillator (WCD). Such switching can introduce impedance imbalances on the measuring inputs that can have a significant effect on the CMRR performance of the preamp.

DESCRIPTION OF THE DRAWING FIGURES

Claimed subject matter is particularly pointed out and distinctly claimed in the concluding portion of the specification. However, such subject matter may be understood by reference to the following detailed description when read with the accompanying drawings in which:

FIG. 1A through FIG. 1H illustrate a diagram of a wearable cardioverter defibrillator (WCD) in accordance with one or more embodiments.

Figure 1A:
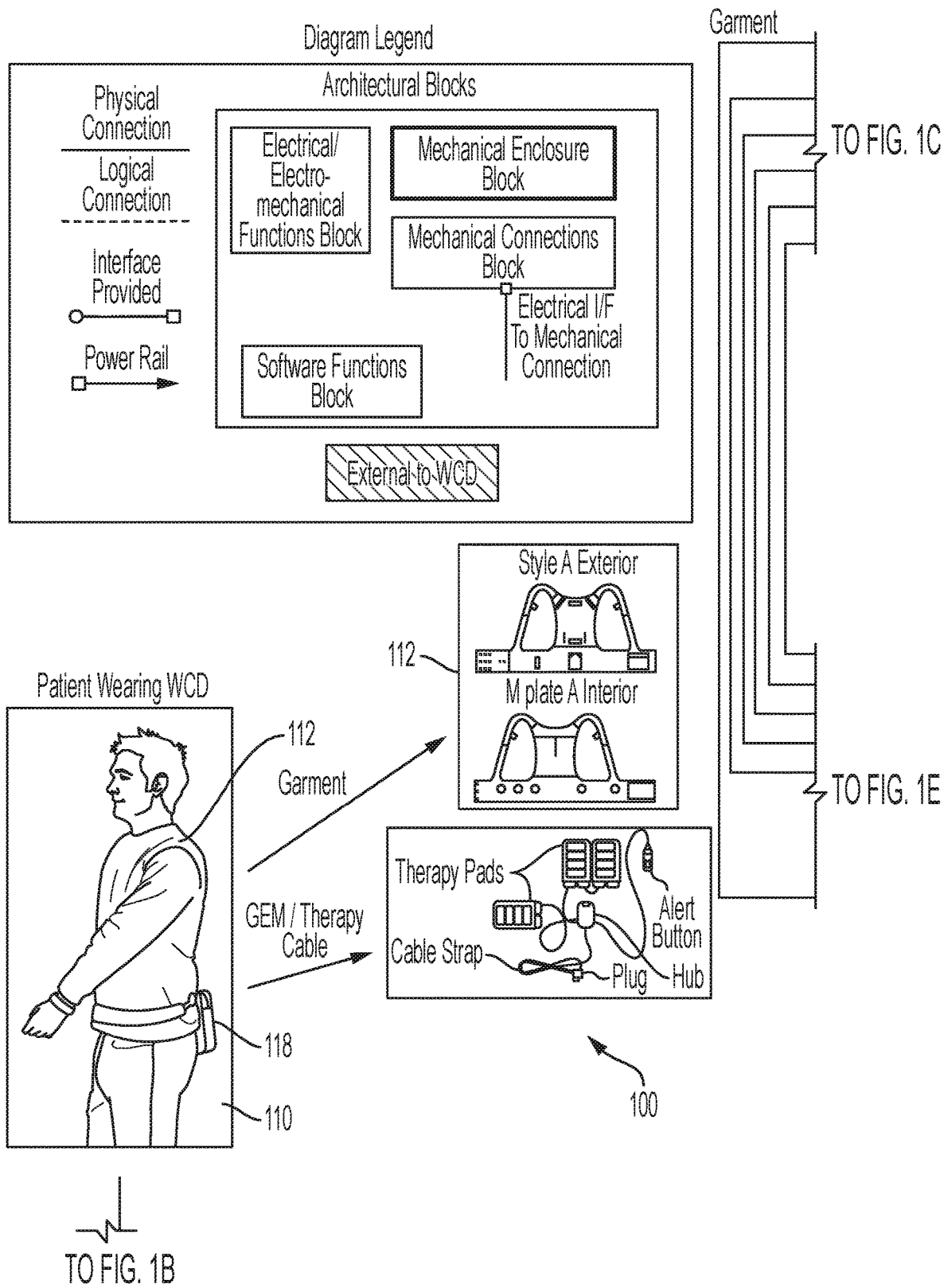
Figure 1B:
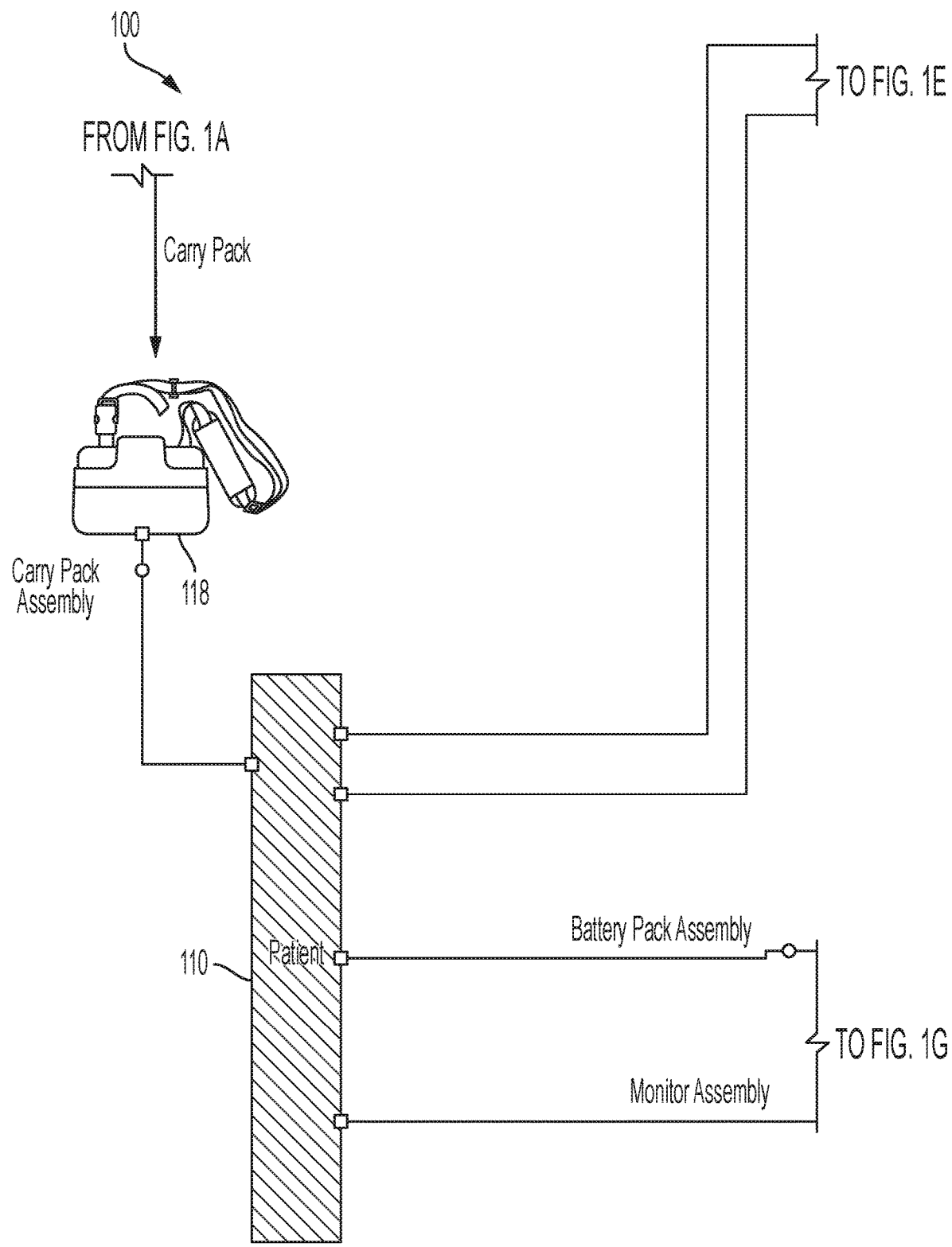

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. It will, however, be understood by those skilled in the art that claimed subject matter may be practiced without these specific details. In other instances, well-known methods, procedures, components and/or circuits have not been described in detail.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. However, coupled may also mean that two or more elements may not be in direct contact with each other, but yet may still cooperate and/or interact with each other. For example, "coupled" may mean that two or more elements do not contact each other but are indirectly joined together via another element or intermediate elements. Finally, the terms "on," "overlying," and "over" may be used in the following description and claims. "On," "overlying," and "over" may be used to indicate that two or more elements are in direct physical contact with each other. It should be noted, however, that "over" may also mean that two or more elements are not in direct contact with each other. For example, "over" may mean that one element is above another element but not contact each other and may have another element or elements in between the two elements. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect. In the following description and/or claims, the terms "comprise" and "include," along with their derivatives, may be used and are intended as synonyms for each other.

Referring now to FIG. 1A through FIG. 1H, a diagram of a wearable cardioverter defibrillator (WCD) in accordance with one or more embodiments will be discussed. A wearable cardioverter defibrillator (WCD) 100 according to embodiments may protect an ambulatory patient by electrically restarting his or her heart if needed. Such a WCD 100 may have a number of components. These components can be provided separately as modules that can be interconnected, or can be combined with other components, and so on.

FIG. 1A depicts a patient 110. Patient 110 may also be referred to as a person and/or wearer, since the patient is wearing components of the WCD 100. Patient 110 can be ambulatory, which means that, while wearing the wearable portion of the WCD 100, patient 110 can walk around and is not necessarily bed-ridden. While patient 110 may be considered to be also a "user" of the WCD 100, this is not a requirement. For instance, a user of the wearable cardioverter defibrillator (WCD) 100 also may be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD 100 according to embodiments can be configured to defibrillate the patient 110 who is wearing and/or carrying the designated parts of the WCD 100. Defibrillating can be by the WCD 100 delivering an electrical charge to the patient's body in the form of an electric shock. The electric shock can be delivered in one or more pulses.

In particular, FIG. 1A through FIG. 1H also depict components of a WCD 100 made according to embodiments. One such component is a support structure or garment 112 that is wearable by ambulatory patient 110. Accordingly, support structure 112 is configured to be worn by ambulatory patient 110 for at least several hours per day, and for at least several days, even a few months. It will be understood that support structure 112 is shown only generically in FIG. 1A through FIG. 1H, and in fact partly conceptually. FIG. 1A through FIG. 1H are provided merely to illustrate concepts about support structure 112 and are not to be construed as limiting how support structure 112 is implemented, or how it is worn.

Support structure 112 can be implemented in many different ways. For example, it can be implemented in a single component or a combination of multiple components. In embodiments, support structure 112 could include a vest, a half-vest, a garment, etc. In such embodiments such items can be worn similarly to analogous articles of clothing. In embodiments, support structure 112 could include a harness, one or more belts or straps, etc. In such embodiments, such items can be worn by the patient 110 around the torso, hips, over the shoulder, etc. In embodiments, support structure 112 can include a container or housing, which even can be waterproof. In such embodiments, the support structure 112 can be worn by being attached to the patient's body by adhesive material, for example as shown and described in U.S. Pat. No. 8,024,037 which is incorporated herein by reference in its entirety. Support structure 112 can even be implemented as described for the support structure of US Pat. App. No. US2017/0056682 which is incorporated herein by reference in its entirety. In such embodiments, the person skilled in the art will recognize that additional components of the WCD 100 can be in the housing of a support structure 112 instead of being attached externally to the support structure 112, for example as described in the US2017/0056682 document. There can be other examples.

FIG. 1E, FIG. 1F, FIG. 1G, and FIG. 1H show a sample external defibrillator 100 comprising a monitor 116, also referred to as a Personal Electrocardiogram (ECG) Monitor (PEM) and a hub 114. In some embodiments, most of the operational circuitry and the energy providing components of WCD 100 may reside within monitor 116 which in turn may couple to support structure 112 via hub 114 which serves to route signals, power, and shock delivery between the patient 110 and monitor 116 via hub 114. In some embodiments, monitor 116 may be contained in a housing such as a carry pack assembly 118 (FIG. 1A and FIG. 1B) carried or worn by the patient 110, and hub 114 may be attached to support structure 112, although the scope of the present subject matter is not limited in this respect. As described in more detail later in this document, some aspects of WCD 100 include a housing and an energy storage module within the housing. As such, in the context of a WCD 100, monitor 116 is sometimes called a main electronics module. The energy storage module in monitor 116 can be configured to store an electrical charge. Other components can cause at least some of the stored electrical charge to be discharged via electrodes through the patient 110 so as to deliver one or more defibrillation shocks through the patient 110.

Figure 1C:
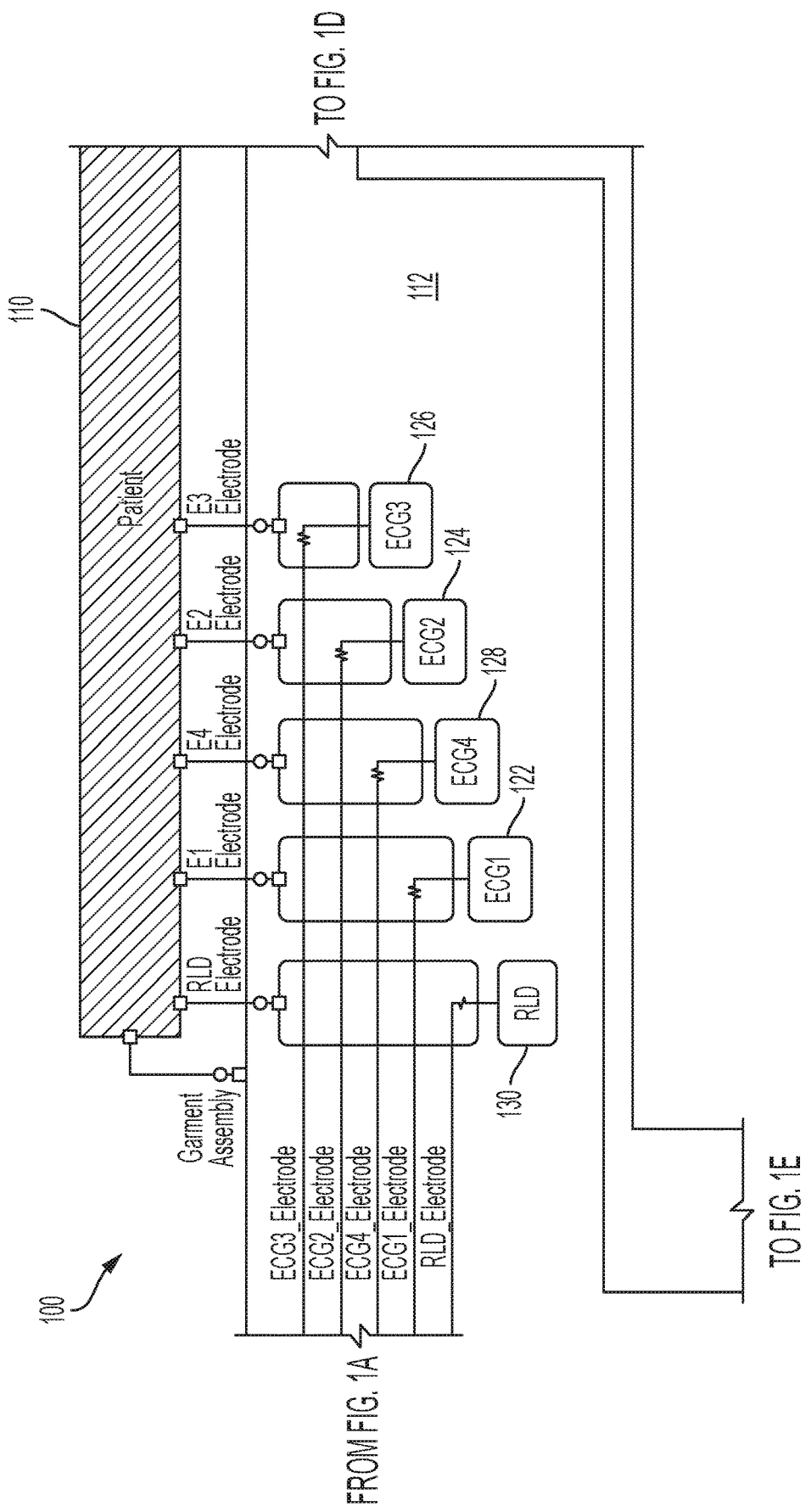
Figure 1D:
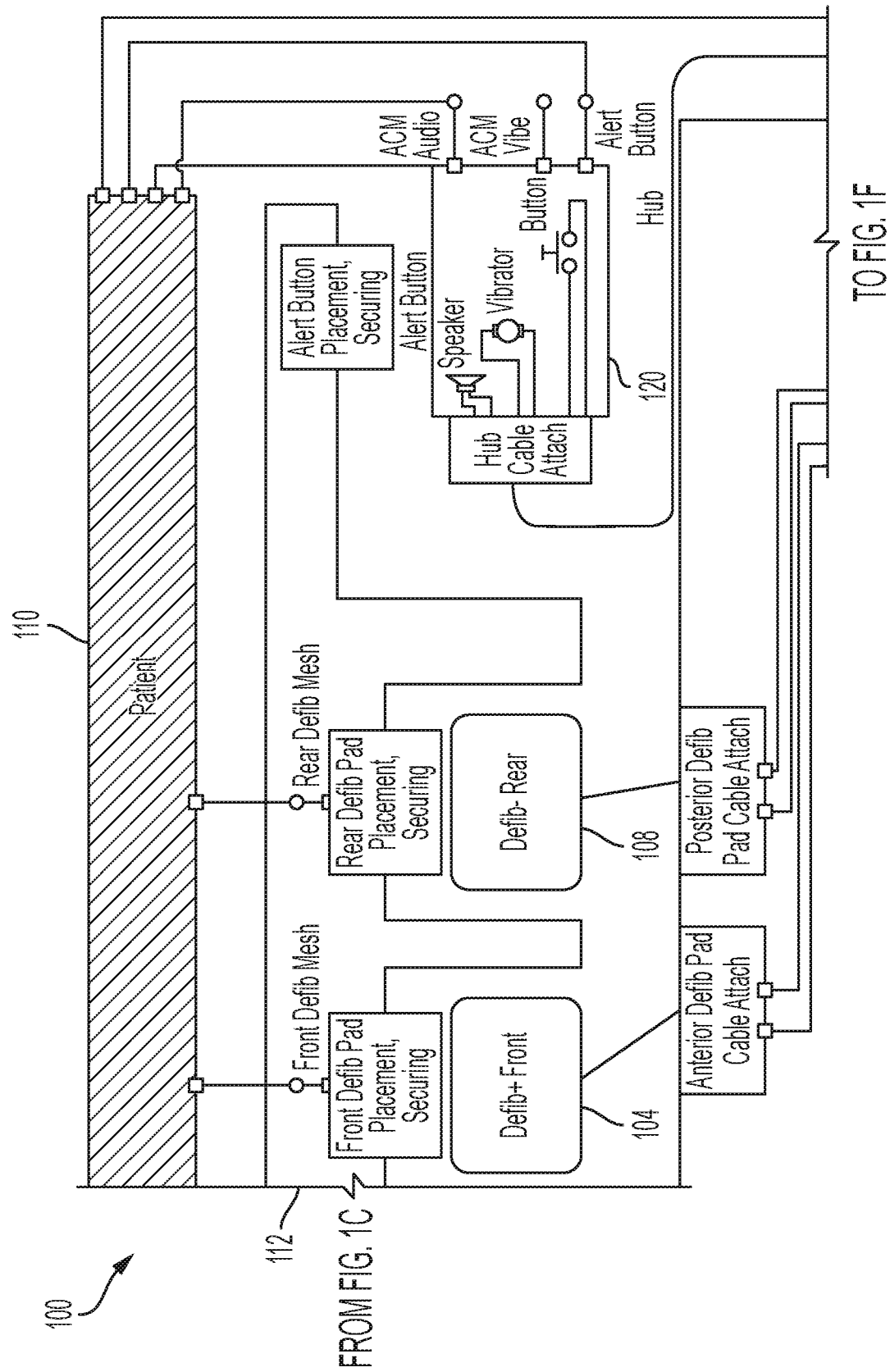

FIG. 1D shows sample defibrillation electrodes such as electrode 104 and electrode 108 which are coupled to monitor 116 via hub 114 via electrode leads. Defibrillation electrodes 104 and 108 can be configured to be worn by patient 110 in a number of ways. For instance, monitor 116 and defibrillation electrodes 104 and 108 can be coupled to support structure 112 either directly or indirectly. In other words, support structure 112 can be configured to be worn by ambulatory patient 110 so as to maintain at least one of electrodes 104 and 108 on the body of ambulatory patient 110 while patient 110 is moving around, etc. The electrode can be thus maintained on the body of the patient 110 by being attached to the skin of patient 110, simply pressed against the skin directly or through garments, etc. In some embodiments the electrode is not necessarily pressed against the skin but becomes biased that way upon sensing a condition that could merit intervention by the WCD 100. In addition, many of the components of monitor 116 can be considered coupled to support structure 112 either directly or indirectly via at least one of defibrillation electrodes 104 or 108.

When defibrillation electrodes 104 and 108 make good electrical contact with the body of patient 110, monitor 116 can administer, via electrodes 104 and 108, a brief, strong electric pulse through the body of the patient 110. Such a pulse is also known as shock, defibrillation shock, therapy, electrotherapy, therapy shock, etc. The pulse is intended to go through and restart the heart of the patient 110 in an effort to save the life of the patient 110. The pulse further can include one or more pacing pulses of lesser magnitude to simply pace the patient's heart if needed, and so on.

Some prior defibrillators may decide whether to defibrillate or not based on an electrocardiogram (ECG) signal of the patient 110. Monitor 116, however, may initiate defibrillation or hold-off defibrillation based on a variety of inputs with the ECG signal merely being one of these inputs, and the scope of the disclosed subject matter is not limited in this respect.

The WCD 100 according to embodiments can obtain data from patient 110. For collecting such data, the WCD 100 optionally may include an outside monitoring device (not shown) external to monitor 116. Such a device may be called an "outside" device because it could be provided as a standalone device, for example not within the housing of monitor 116. An outside monitoring device can be configured to sense or monitor at least one local parameter. A local parameter can be a parameter of patient 110, a parameter of the WCD 100, or a parameter of the environment, as will be described later in this document.

For some of these parameters, an outside monitoring device may include one or more sensors or transducers. Each one of such sensors can be configured to sense a parameter of patient 110, and to render an input responsive to the sensed parameter. In some embodiments the input is quantitative, such as values of a sensed parameter. In other embodiments the input is qualitative, such as informing whether or not a threshold is crossed, and so on. Sometimes these inputs about patient 110 are also called physiological inputs and patient inputs. In embodiments, a sensor can be construed more broadly, as encompassing many individual sensors.

Optionally, an outside monitoring device can be physically coupled to support structure 112. In addition, an outside monitoring device may be communicatively coupled with other components that are coupled to support structure 112. Such communication can be implemented by a communication module, as will be deemed applicable by a person skilled in the art in view of this description.

In some embodiments, one or more of the components of the shown WCD 100 may be customized for patient 110. This customization may include a number of aspects. For instance, support structure 112 can be fitted to the body of patient 110. For another instance, baseline physiological parameters of patient 110 can be measured, such as the heart rate of patient 110 while resting, while walking, motion detector outputs while walking, etc. The measured values of such baseline physiological parameters can be used to customize the WCD 100 in order to make its diagnoses more accurate, since patients' bodies differ from one another. Of course, such parameter values can be stored in a memory of the WCD 100, and so on. Moreover, a programming interface can be made according to embodiments, which receives such measured values of baseline physiological parameters. Such a programming interface may input automatically in the WCD 100 these, along with other data.

Figure 1E:
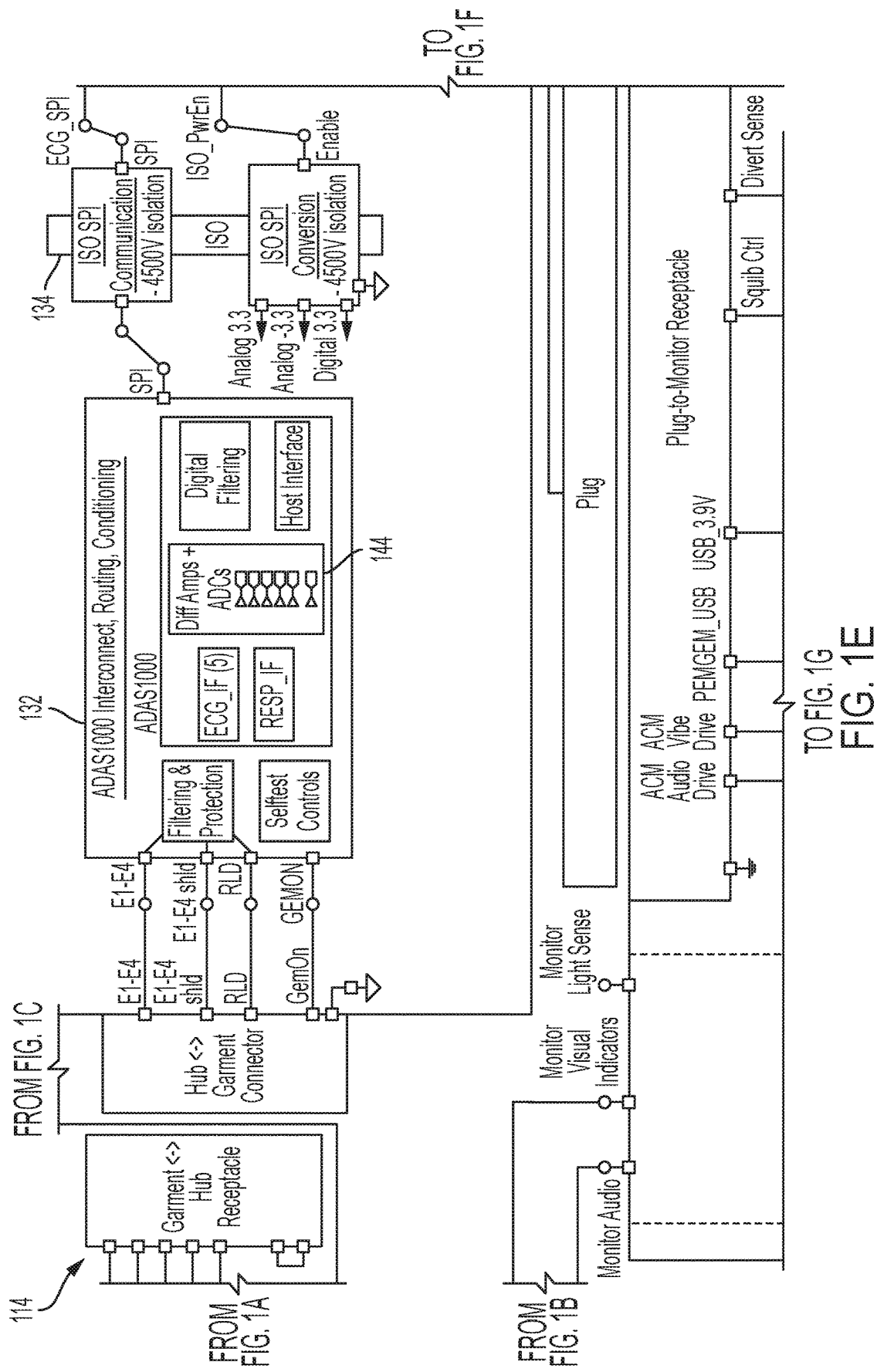
Figure 1G:
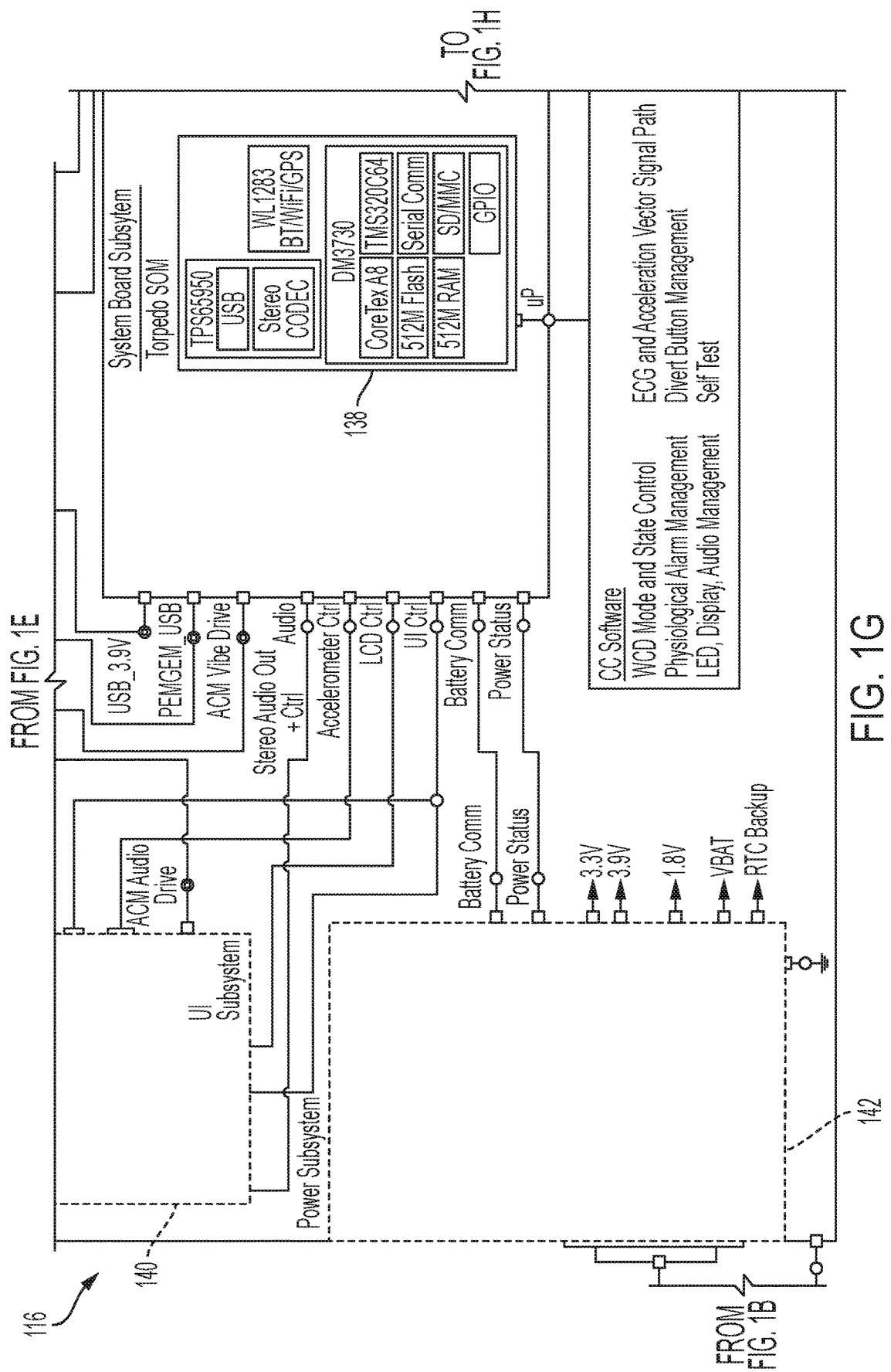
Figure 1H:
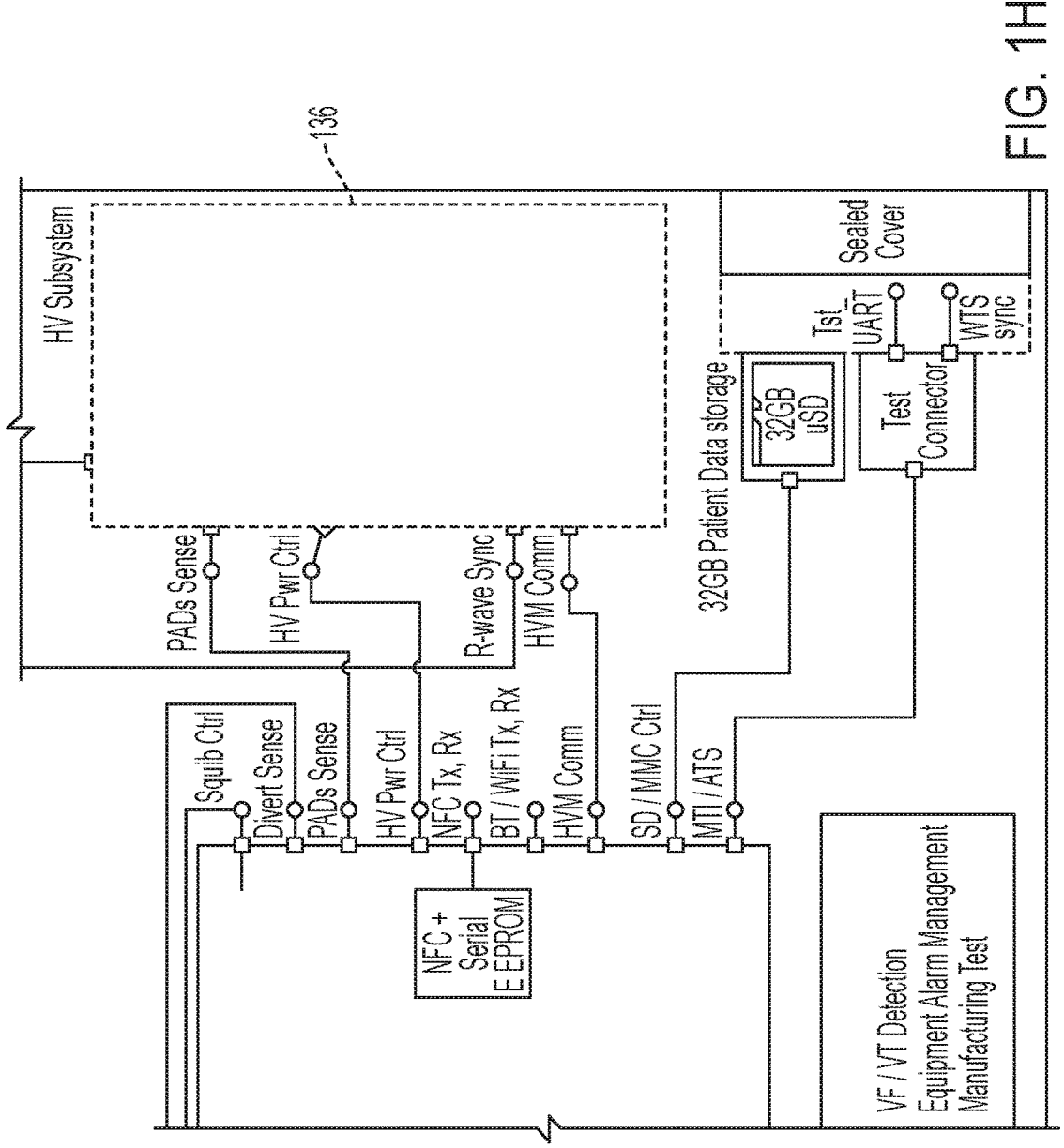

In one or more embodiments, for example as shown in FIG. 1C, WCD 100 may comprise the following architecture. Support structure 112 can comprise a garment such as a vest to be worn by the patient 110. Support structure 112 can include ECG electrodes such as electrode (ECG1) 122, electrode (ECG2) 124, electrode (ECG3) 126, and electrode (ECG4) 128, and right-leg drive (RLD) electrode 130. The ECG and RLD electrodes and defibrillation electrodes 104 and 108 can connect to hub 114 which includes front end electronics, interconnects, conditioning, and routing for the electrodes. Hub 114 can be attached to the support structure (vest or garment) 112 on the back of the support structure 112 so that the hub 114 is positioned on the patient's back when the patient 110 is wearing the garment. The circuitry of hub 114, for example as shown in FIG. 1E and FIG. 1F, includes an ECG acquisition system which uses five communication lines E1_ECG, E2_ECG, E3_ECG, E4_ECG, and RLD to connect to the ECG electrodes 122-128 including the RLD electrode 130 of support structure 112. The ECG electrodes connect to the patient's skin to obtain ECG signals from the patient 110. In addition, there are four shield lines and a cable sense line. Hub 114 can include a preamplifier 132 and an isolation barrier 134 which will be discussed in more detail with respect to FIG. 4A and FIG. 4B, below.

An alert button 120 can connect to hub 114 and may include a speaker and vibrator. In addition, alert button 120 can include a button to allow the patient 110 to divert or abort a defibrillator shock in the event the patient 110 believes an impending shock to be unnecessary. Alert button 120 can also be referred to as a stop button, a divert button, or a user interface, and the scope of the disclosed subject matter is not limited in this respect. Hub 114 can connect the electrodes of support structure 112 and the alert button 120 to monitor 116 which houses the main electronics and other components of WCD 100, which may be contained within a carry pack assembly 118 that may be carried by the patient 110 or worn on the patient's hip. Monitor 116 may include the battery 142, the defibrillator capacitor 136, user interface 140, and main processor 138 of WCD 100.

In some embodiments, the processor 138 is a TORPEDO System on Module (SOM) available from Logic PD, Inc. of Eden Prairie, Minn., USA, although the scope of the disclosed subject matter is not limited in this respect. Processor 138 is used to run some portions of the shock decision algorithm to determine when WCD 100 should apply a shock to the patient 110 and is capable of applying filters on four channels simultaneously while also controlling wireless communications and other functions of WCD 100. In some embodiments, at least some portions of the shock algorithm may be run by a controller or processor 410 located in the hub 114 as shown in and described with respect to FIG. 4A and FIG. 4B, below, and the scope of the disclosed subject matter is not limited in this respect. One example portion of the shock algorithm that can be executed by the processor 410 in the hub 144 is a gatekeeper function, and the scope of the disclosed subject matter is not limited in this respect. Monitor 116 also may include a user interface (UI) 140 to allow a user to control and interact with WCD 100. In some embodiments, the user may stop or divert an impending shock via the user interface 140, or via the alert button 120. Monitor 116 also includes a speaker that provides audible alerts and some status indicators.

Figure 2:
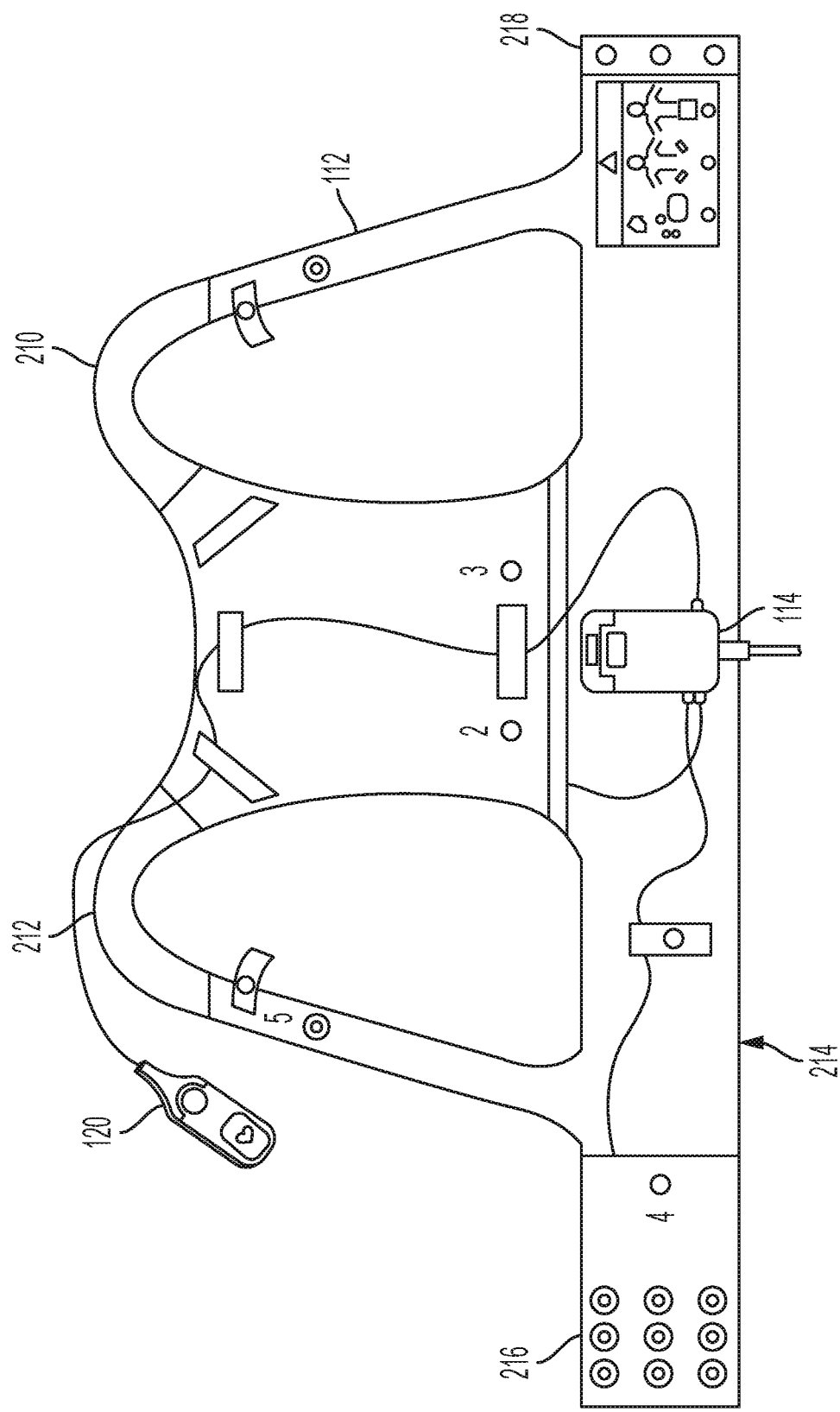
FIG. 2 is a diagram of a back view of a garment of a WCD in accordance with one or more embodiments.

Referring now to FIG. 2, a diagram of a back view of a garment of a WCD in accordance with one or more embodiments will be discussed. The garment shown in FIG. 2 comprises the support structure 112 of FIG. 1A, FIG. 1C, and FIGS. 1D and 1s shown in a vest configuration. The garment may include shoulder straps 210 and 212 to be placed over the shoulders of the patient 110 and for support of the support structure 112. The garment may include a belt portion 214 to be fastened around the waist of the patient 110. The belt portion 214 may include various fasteners 216 and 218, for example closure snaps, to allow the garment to be fitted to different sized users. Hub 114 can be attached to the back side of the garment, for example on or near the belt portion 214, to allow various cables to be connected to hub 114 including alert button (divert button) 120 and cabling to connect to the therapy/defibrillator electrodes and ECG electrodes (not shown). In some embodiments, support structure 112 can comprise a vest-like fabric garment to be worn on the patient's body underneath an outer shirt or other clothing to allow the electrodes to contact the patient's skin and hold the electrodes in close proximity to and/or direct contact with the patient's skin. Such an arrangement allows for the WCD 100 to obtain ECG signals from the patient and to allow the shock to be applied to the patient 110 when appropriate.

Figure 3:
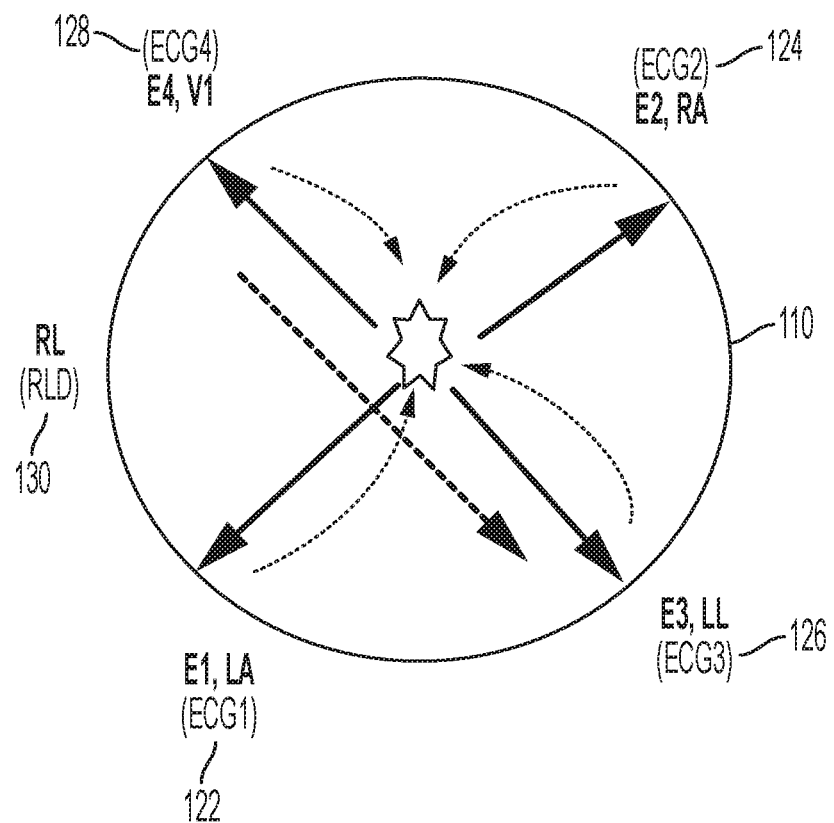
FIG. 3 is a diagram of a WCD application that includes four monitoring electrodes E1-E4 spread out around the body along with the driven electrode (RLD) in accordance with one or more embodiments.

FIG. 3 is a diagram of a WCD application that includes four monitoring electrodes E1-E4 spread out around the body along with the driven electrode (RLD) in accordance with one or more embodiments. FIG. 3 schematically illustrates an embodiment WCD application which includes four monitoring electrodes E1-E4, corresponding to electrodes ECG1 122, ECG2 124, ECG3 126, and ECG4 128 as shown in FIG. 1C and provided as inputs to preamp 132 as shown in FIG. 1E. The electrodes can be spread out around the patient's body along with the driven electrode (RLD) 130 as shown in FIG. 1C and FIG. 1E. In such embodiments, the WCD 100 is enabled to monitor the impedance both between electrodes E1 and E2 as well as between electrodes E3 and E4.

The impedance measurements can be used to assist in determining which pair of electrodes is likely to provide the best ECG signals because the electrode pair's corresponding impedance channel is changing less. Smaller changes in the impedance channel signal can be indicative of less motion occurring in the areas where the monitored electrodes are placed on the patient's body. In another example embodiment, the impedance signal can be analyzed to determine a patient's respiration. In these embodiments, both impedance signals can be analyzed for both noise content and signal amplitude, and the higher quality signal can then be selectively monitored for detecting respiration. In accordance with one or more embodiments as discussed further below, any imbalance in the input capacitive loading on each ECG input can be compensated by adding fixed capacitance to any or all channels to balance the capacitive loading.

Some embodiments can involve switching all of the impedance measurement circuitry between the two pairs of electrodes. This adds additional switches for both switching between the electrodes and switches to balance the capacitance on all four lines. Some embodiment can have a topology where at least parts, but not all, of the same circuitry are used to measure impedances of multiple electrode pairs. Such an arrangement can result in the capacitive loading varying as a result of changing the preamp topology with a concomitant decrease in the common mode rejection ratio (CMRR) in the differential input circuitry of preamp 132.

Some embodiments overcome the lack of being able to switch which pair of ECG electrodes out of a plurality of pairs is being monitored for impedance while at the same time compensating for any input capacitance imbalance by automatically switching in or out capacitors to maintain balanced input capacitance loading resulting in maintaining a high CMRR. In one embodiment, a topology for preamp 132 can be provided to monitor four ECG electrodes along with a driven electrode, commonly referred to as the Right Leg Drive (RLD). To minimize circuit complexity, this embodiment can include only circuitry to monitor one impedance channel, the impedance between two electrodes, and additional switching to allow this circuitry to be used to measure the impedance of a completely separate pair of electrodes.

Some embodiments are directed to compensating for changing input capacitance to an ECG preamp 132 due to preamp topology changes, by switching in or out fixed capacitances. According to some embodiments, one such topology change can include enabling or disabling measuring impedance between two inputs to the preamp 132, nominally between two ECG electrodes on the patient's body. According to other embodiments, another topology change can include switching which two electrodes out of a plurality of three or more electrodes are being used as inputs for the impedance measurement circuit. The benefit of these embodiments is the ability to maintain a high Common Mode Rejection Ration (CMRR) on the ECG inputs to preamp 132 during topology changes which would normally result in a reduced CMRR and thus reduced ECG signal quality. An example preamp 132 for receiving switched electrode inputs with impedance balancing is shown in and described with respect to FIG. 4A and FIG. 4B, below.

Figure 4A:
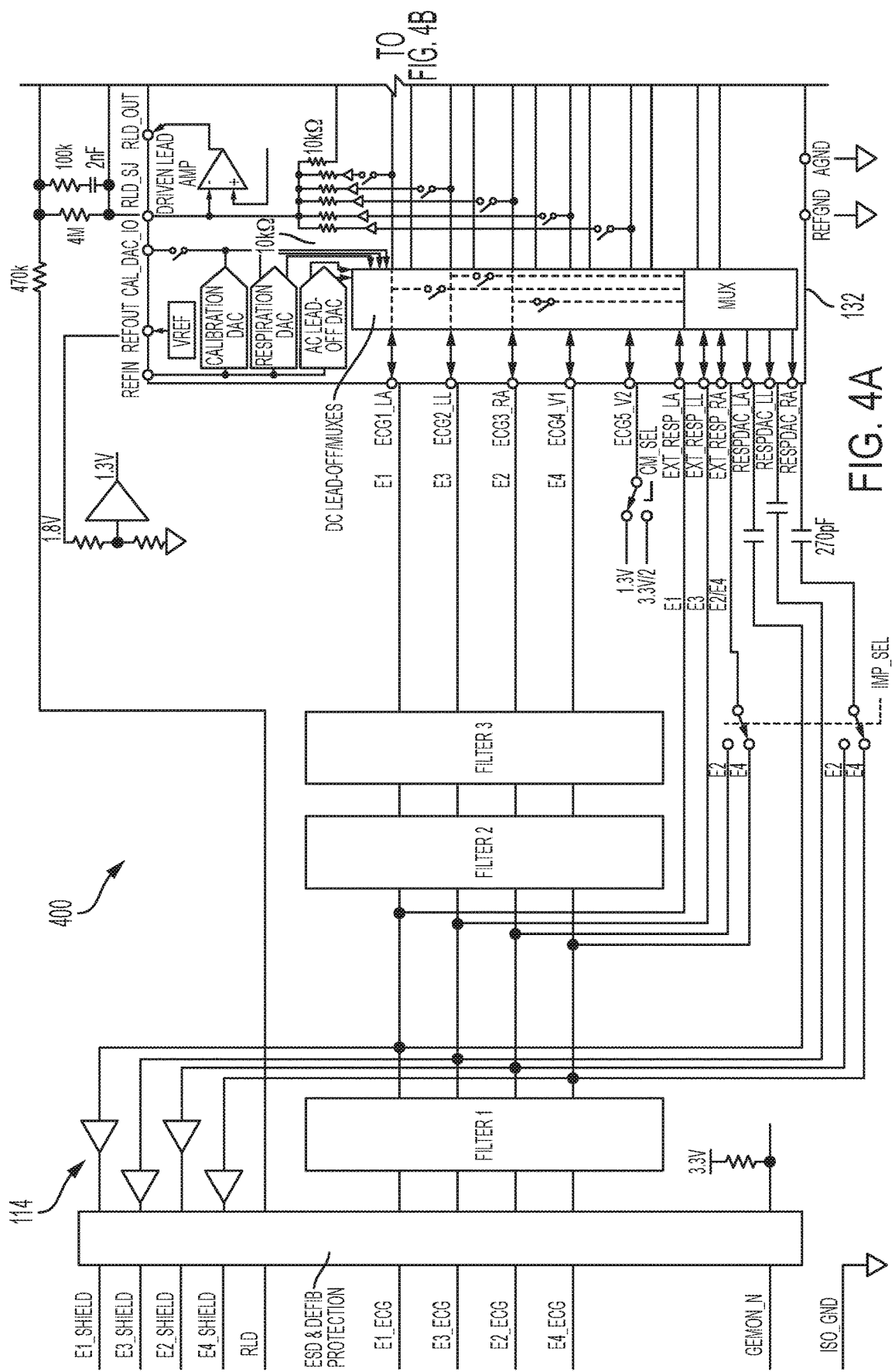
FIG. 4A and FIG. 4B illustrate a diagram of a front end of an ECG device used in a WCD in accordance with one or more embodiments.
Figure 4B:
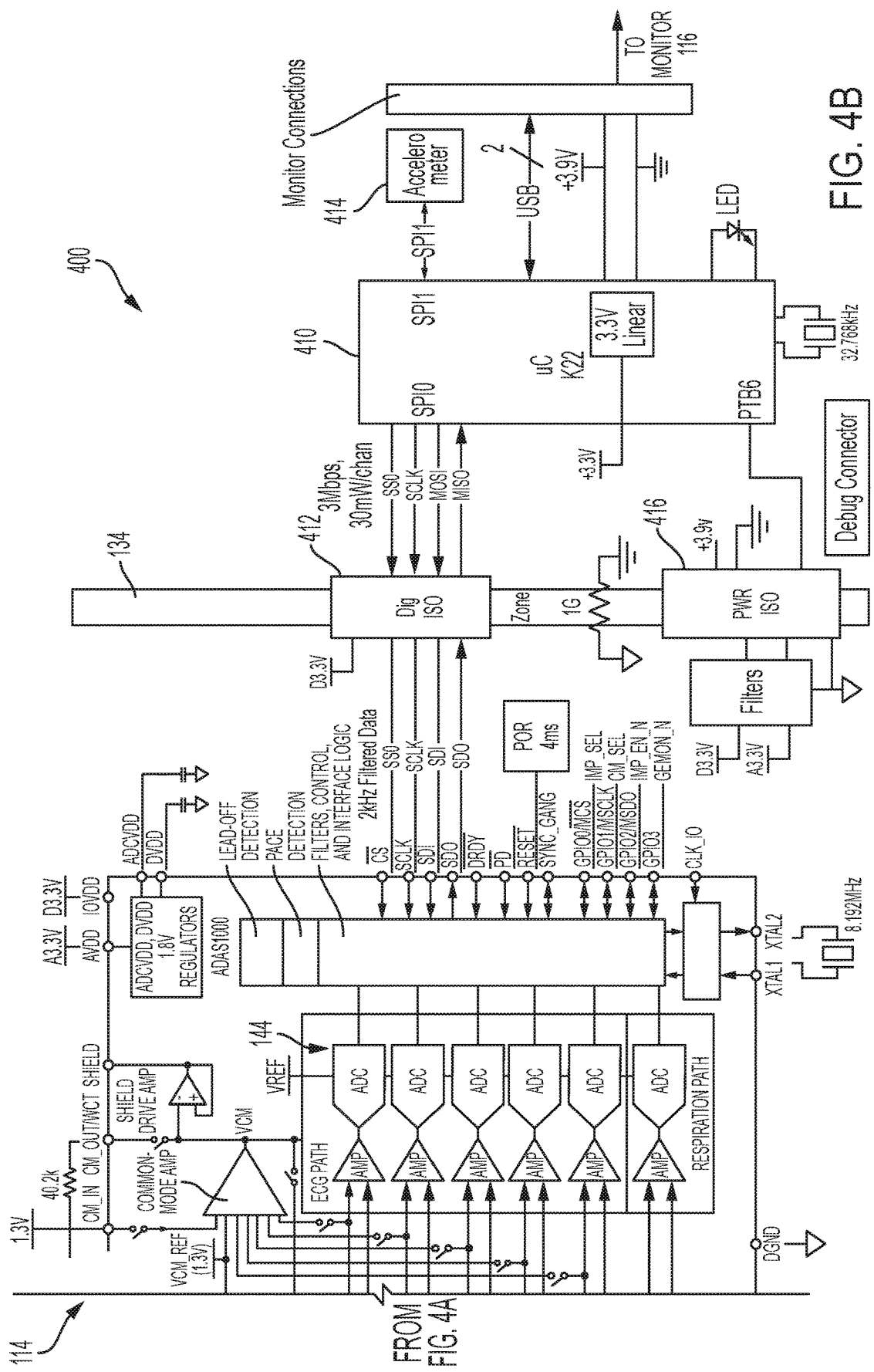

Referring now to FIG. 4A and FIG. 4B, a diagram of a front end of an ECG device used in a WCD in accordance with one or more embodiments will be discussed. The ECG front end circuitry 400 in the hub 114 can comprise a preamplifier 132 that is isolated from processor 410 via an isolation barrier 134. In some embodiments, preamplifier 132 can comprise an ADAS1000 preamplifier available from Analog Devices, Inc. of Norwood, Mass., USA, and processor 410 can comprise a KINETIS K22 microcontroller available from NXP Semiconductors N.V. of Eindhoven, The Netherlands, although the scope of the disclosed subject matter is not limited in this respect.

Isolation barrier 134 serves to isolate the preamplifier from processor 410 and the rest of the WCD 100 system. Signals from the ECG electrodes are provided to the preamplifier 132 which converts the ECG signals into digital signals using analog-to-digital converters (ADCs) 144. The digital signals are passed from the preamplifier 132 through the isolation barrier 134 to processor 410 through digital isolator 412. The processor 410 has a Universal Serial Bus (USB) interface that goes to the monitor 116 and the rest of the WCD 100 system. The isolation barrier 134 can also include a power isolator 416 to isolate the power provided to the preamplifier 132 from the power provided to the processor 410.

In some embodiments, ECG front end circuitry 400 includes an isolation barrier configured to electrically isolate preamplifier 132 from the main circuit ground to which other circuits of WCD 100 are connected, for example the circuitry of monitor 116. Isolation barrier 134 may in turn include an additional circuit ground isolated from the main circuit ground. This isolation enhances the quality of the acquired ECG data, which may result in fewer false alarms and increased patient safety. Non-isolated ECG acquisition systems are susceptible to environmental noise sources such as 60 Hz fields in the vicinity of the WCD 100. Patient leakage currents could be difficult to control. Further, electrical noise generated by switch mode power supplies or high voltage charging circuits could couple into the ECG acquisition system of the WCD 100. Thus, preamplifier 132 may have its own ground reference which is different from and isolated from the ground reference used by processor 410 and the remaining circuits of the WCD 100 including the circuits of monitor 116.

In one or more embodiments, isolation barrier 134 can include digital isolator 412 and power isolator 416. Digital isolator 412 can comprise any one or more types of isolators such as galvanic couplers, such as provided by inductance or capacitance devices, such as an isolation transformer or an isolation capacitor, or by a non-electrical means, such as an opto-isolator comprising for example photodiodes and/or phototransistors, and the scope of the disclosed subject matter is not limited in this respect. In some embodiments, the isolation barrier 134 provides protection from the voltages applied by the defibrillator discharge circuit provided by monitor 116. Power isolator 416 can be configured to transfer power across the isolation barrier 134 without providing DC coupling across the isolation barrier 134, for example using a transformer, although the scope of the disclosed subject matter is not limited in this respect. In one or more embodiments, isolation barrier 134 can be embodied by an isolating circuit as described in U.S. Pat. No. 10,322,291 which is incorporated herein by reference in its entirety.

In one or more embodiments, the preamplifier 132 has four single-ended ECG inputs receiving the ECG signals, an active right-leg drive, a wide dynamic range, and direct-current (DC) leads-off detection. In some embodiments, preamplifier 132 supports DC leads-off detection, and in other embodiments preamplifier supports alternating-current (AC) leads-off detection, or both, and the scope of the disclosed subject matter is not limited in this respect. In some embodiments, preamplifier 132 includes circuitry to measure the patient impedance values between the ECG electrodes. These impedance values can be used to detect the patient's respiration, for example as shown in U.S. application Ser. No. 15/792,860 filed Oct. 25, 2017, published as US 2018/0117299 A1, and which is incorporated herein by reference in its entirety. As shown in FIG. 4A, in some embodiments the lines E1_ECG, E2_ECG, E3_ECG, and E4_ECG connect to the ECG electrodes in the garment or support structure 112. The RLD line connects to another electrode that is used as a right-leg drive. The preamplifier 132 digitizes the ECG signals so that digitized values of the ECG signals, not the actual ECG signals, are passed through the isolation barrier 134 to the processor 410. The ECG front end circuitry 400 is all contained in a small module comprising the hub 114 that is attached to the garment or support structure 112, for example in the middle of the patient's back as shown in FIG. 2A. In other embodiments the hub 114 may be attached to various other locations on the garment or support structure 112 other than the middle of the patient's back. For example, the hub 114 may be located at a shoulder area, a side area, or a front or chest area of the patient 110 when the patient 110 is wearing the support structure, and the scope of the disclosed subject matter is not limited in this respect. In some embodiments, ECG front end circuitry 400 also can include a motion sensor 414 such as, for example, a 3-axis accelerometer in the same package comprising the hub 114. In some embodiments, the microprocessor sends the ECG signals, the ECG leads-off signals, and the accelerometer signals over a USB connection to monitor 116 which performs most of the signal processing of the WCD 100. In some embodiments, ECG leads-off is detected by injecting a low-level DC current into each electrode. The return path for this current is through the RLD line. If an electrode becomes disconnected from the patient 110, the current injection causes the DC voltage at the electrode to hit the upper rail. When an electrode voltage hits the rail, it is flagged as being "off."

In one or more embodiments, the isolation barrier 134 shown in FIG. 4B may contribute to the enhanced performance of the WCD system because the isolation barrier 134 operates to greatly enhance the common-mode rejection of the WCD 100. In some embodiments, the preamplifier 132 has an input voltage range of 0 V to 2.6 V. The ground reference is nominally at 1.3 V. Any channel with a DC level of greater than 2.4 V or less than 0.2 V can be considered "off". This arrangement gives the ECG front end circuitry 400 a usable dynamic range of +/−1.1 V, which is relatively large compared to the size of the cardiac signal of interest, which is typically around 1 mV. Such a wide dynamic range allows at least most of the ECG filtering to happen in software without the signal being clipped. Digital filters can be very effective at removing artifacts and may contribute to the enhanced false positive performance of the WCD 100 according to embodiments as described herein.

In some embodiments, the preamplifier 132 has a very high sample rate so the anti-aliasing filters have little impact on the ECG signal quality. The preamplifier 132 is to provide data to the processor 410 at a 2 kHz rate with a bandwidth from DC to 250 Hz. The software down samples to 500 Hz and further bandlimits the signal for algorithm processing. It should be noted that aspects of embodiments of the ECG front end circuitry 400 are disclosed in U.S. application Ser. No. 15/365,801 filed Nov. 30, 2016 which is incorporated herein by reference in its entirety.

Figure 5:
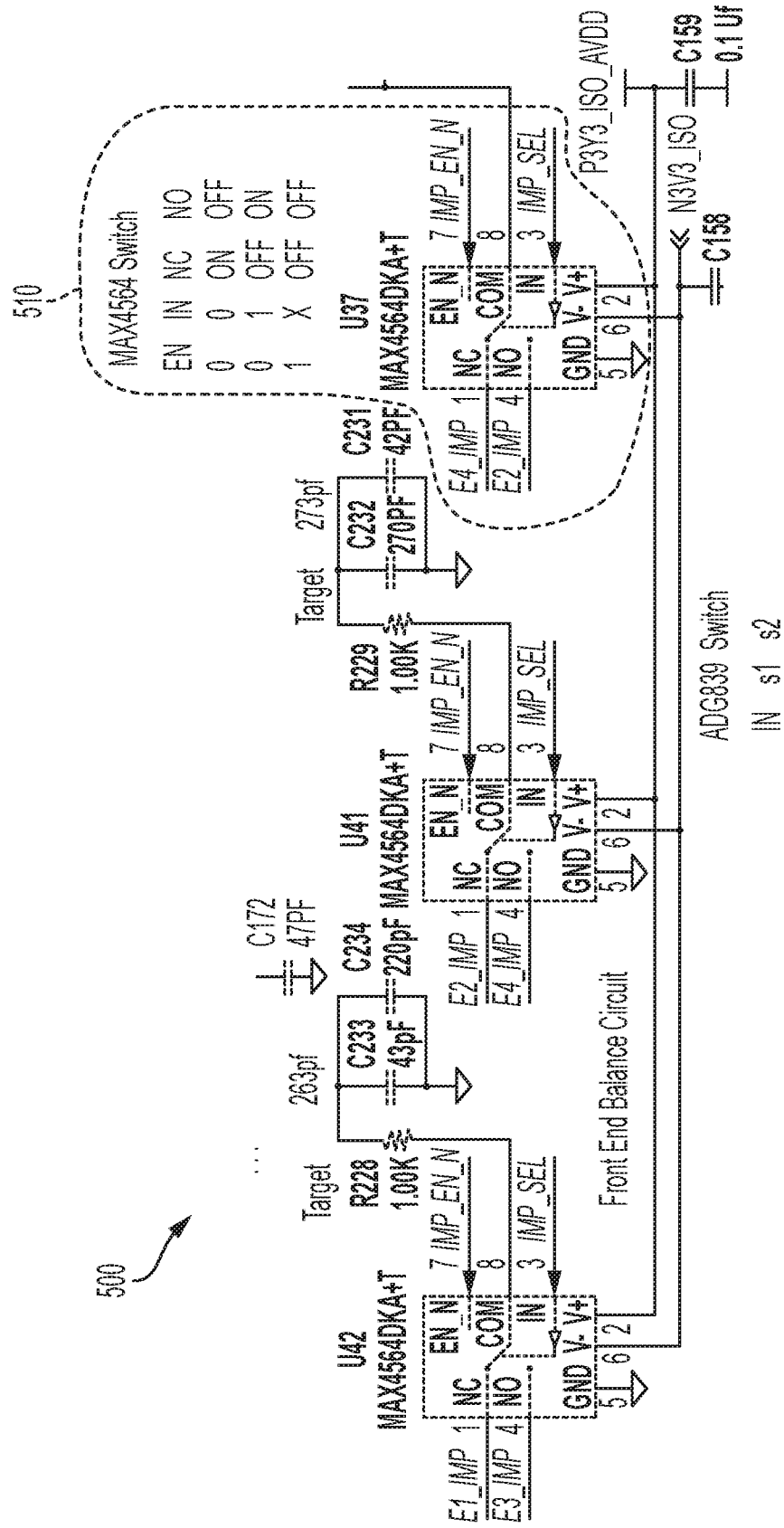
FIG. 5 is diagram of a switching portion of an impedance measurement circuit in accordance with one or more embodiments.

FIG. 5 is diagram of a switching portion of an impedance measurement circuit in accordance with one or more embodiments. As shown in FIG. 5, switching between pairs of electrodes can be accomplished by switching part of the impedance measurement circuit 500 between the two pairs of electrodes, for example between electrodes E1 and E2 or between electrodes E3 and E4. The switching portion 510 of the impedance measurement circuit is shown as including for example switch U37. In switching part of the impedance measurement circuit 500 from one pair of electrodes to another pair, the topology of preamp 132 can change in such a way that the input capacitive loading also changes. To overcome this imbalance, additional switches can be added to enable adding or removing capacitors having carefully determined capacitance values to each channel as required. Such additional switches and capacitors are shown in and described with respect to FIG. 6, below.

Figure 6:
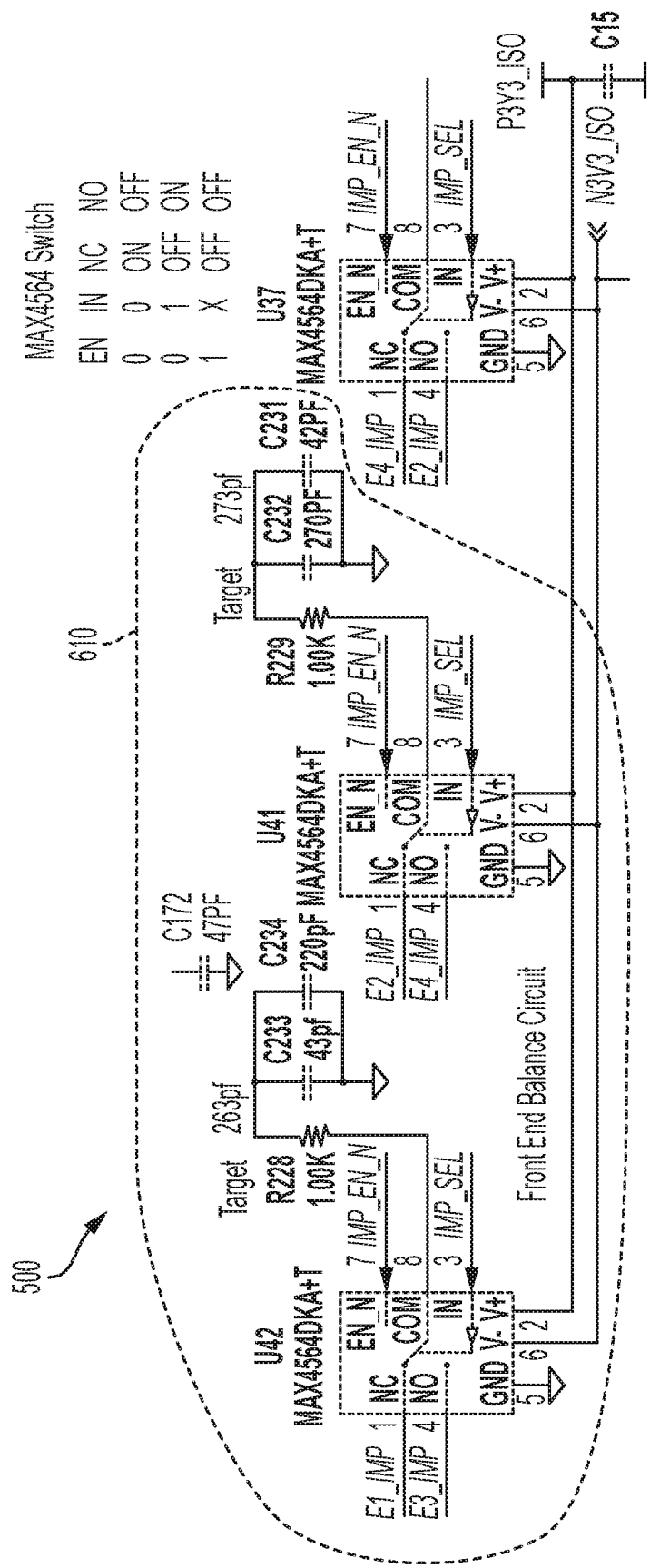
FIG. 6 is a diagram of a front end balance circuit to enable adding or removing capacitors to address capacitance imbalance in accordance with one or more embodiments.

FIG. 6 is a diagram of a front end balance circuit to enable adding or removing capacitors to address capacitance imbalance in accordance with one or more embodiments. The embodiment shown in FIG. 6 enables using parts of the impedance measurement circuit 500 for measuring the impedance of two separate pairs of electrodes while maintaining a balanced capacitive loading on each ECG input. The front end balance circuit 610 can include, for example, switches U41 and U42 for selectively switching in or out balance capacitors C231 and C232 and balance capacitors C233 and C234. The determination of the values for the balance capacitors is described below.

In one or more embodiments, ECG input balance is provided when the impedance measurement function is enabled at the inputs of the preamp 132. Under some modes of operation, the AFE 400 of WCD 100 can operate the ECG circuitry when the impedance measurement function is active. Since that impedance measurement circuit applied to a first pair of electrodes can change the impedance between the first pair of electrodes compared to the impedance of the other pair of electrodes to which the impedance measurement circuit is not applied, in such embodiments balancing capacitors can be introduced to achieve or otherwise restore or maintain the balance between the ECG channels at the inputs of preamp 132. When the impedance measurement function is enabled, the analog switches U37, U41 and U42 are enabled by setting the signal line IMP_EN_N low.

In one or more embodiments, capacitive Balancing for ECG Channel E1 and E2 can be determined as follows. Table 1 and Table 2 below list every capacitance value in picofarads (pF) on the ECG signal path when the impedance measurement, either Imp34 or the Imp12, is enabled. The capacitor names are explained below.

U37_in: input capacitance of U37
U37_out: output capacitance of U37
DrvOn: driving cap hanging on ECG path when impedance pair is selected
U24_in: input capacitance of U24
DrvOff: driving cap+output capacitance of ADAS1000 internal switch when impedance pair is off
PathC: total capacitance on the ECG path
Comp: external compensation capacitance
Total: total capacitance, the sum of PathC and Comp
Delta: difference of capacitance between the ECG differential pair In order to minimize unbalance capacitance in the column "Delta", the following compensation capacitance values can be selected: 271 pF on ECG Channel E1 and 281 pF on ECG Channel E2. The worst ECG pair E34 below has the remaining unbalanced capacitance of 14 pF.

TABLE 1

Calculation of Balancing Capacitance for E1 and E2

| ECG | Lead | U37_in | U37_out | DrvOn | U24_in | DrvOff | PathC | Comp | Total | Delta |
|---|---|---|---|---|---|---|---|---|---|---|
| E24 | E2 | 6 | 0 | 0 | 0 | 0 | 6 | 281 | 287 | −7 |
|  | E4 | 6 | 8 | 270 | 10 | 0 | 294 | 0 | 294 |  |
| E34 | E3 | 0 | 0 | 270 | 10 | 0 | 280 | 0 | 280 | −14 |
|  | E4 | 6 | 8 | 270 | 10 | 0 | 294 | 0 | 294 |  |
| E14 | E1 | 0 | 0 | 0 | 10 | 6 | 16 | 271 | 287 | −7 |
|  | E4 | 6 | 8 | 270 | 10 | 0 | 294 | 0 | 294 |  |

TABLE 1-continued

Calculation of Balancing Capacitance for E1 and E2

| ECG | Lead | U37_in | U37_out | DrvOn | U24_in | DrvOff | PathC | Comp | Total | Delta |
|---|---|---|---|---|---|---|---|---|---|---|
| E23 | E2 | 6 | 0 | 0 | 0 | 0 | 6 | 281 | 287 | 7 |
|  | E3 | 0 | 0 | 270 | 10 | 0 | 280 | 0 | 280 |  |
| E21 | E2 | 6 | 0 | 0 | 0 | 0 | 6 | 281 | 287 | 0 |
|  | E1 | 0 | 0 | 0 | 10 | 6 | 16 | 271 | 287 |  |
| E31 | E3 | 0 | 0 | 270 | 10 | 0 | 280 | 0 | 280 | −7 |
|  | E1 | 0 | 0 | 0 | 10 | 6 | 16 | 271 | 287 |  |

In one or more embodiments, capacitive balancing for ECG Channel E3 and E4 can be determined as follows. Using the same definitions and the approach as described above, Table 2 shows the optimized capacitive compensations for the ECG path E3 and E4 can be: 271 pF on ECG Channel E3 and 281 pF on ECG Channel E4. The worst ECG pair E12 in Table 2 below has the remaining unbalanced capacitance of 14 pF.

TABLE 2

Calculation of Balancing Capacitance for E3 and E4

| ECG | Lead | U37_in | U37_out | DrvOn | U24_in | DrvOff | PathC | Comp | Total | Delta |
|---|---|---|---|---|---|---|---|---|---|---|
| E24 | E2 | 6 | 8 | 270 | 10 | 0 | 294 | 0 | 294 | 7 |
|  | E4 | 6 | 0 | 0 | 0 | 0 | 6 | 281 | 287 |  |
| E34 | E3 | 0 | 0 | 0 | 10 | 6 | 16 | 271 | 287 | 0 |
|  | E4 | 6 | 0 | 0 | 0 | 0 | 6 | 281 | 287 |  |
| E14 | E1 | 0 | 0 | 270 | 10 | 0 | 280 | 0 | 280 | −7 |
|  | E4 | 6 | 0 | 0 | 0 | 0 | 6 | 281 | 287 |  |
| E23 | E2 | 6 | 8 | 270 | 10 | 0 | 294 | 0 | 294 | 7 |
|  | E3 | 0 | 0 | 0 | 10 | 6 | 16 | 271 | 287 |  |
| E21 | E2 | 6 | 8 | 270 | 10 | 0 | 294 | 0 | 294 | 14 |
|  | E1 | 0 | 0 | 270 | 10 | 0 | 280 | 0 | 280 |  |
| E31 | E3 | 0 | 0 | 0 | 10 | 6 | 16 | 271 | 287 | 7 |
|  | E1 | 0 | 0 | 270 | 10 | 0 | 280 | 0 | 280 |  |

In one or more embodiments, implementation of capacitive balancing can be as follows. To make the best balance of the capacitance between all ECG differential pairs, the results obtained above can be combined, and the following balance capacitors can be selected: 271 pF for ECG signal path E1 and E2, and 281 pF for ECG signal path E3 and E4. Thus, when the impedance measurement circuit is applied to electrode pairs E1 and E2, a balance capacitance of 281 pF can be applied to electrode pairs E3 and E4. Likewise, when the impedance measurement circuit is applied to electrode pairs E3 and E4, a balance capacitance of 271 pF can be applied between electrodes E1 and E2. The minimum capacitive differences are given in column "Delta" in Table 1 and Table 2 above. The rows for E3 and E4 in Table 1 and for E2 and E1 in Table 2 are the worst cases of the ECG capacitive balance. Ideally for E1 and E3, the balance capacitor should be 271 pF minus 8 pF, or 263 pF, implemented as C233 and C234, combined in parallel to achieve the overall desired capacitance value, as shown in FIG. 5 and FIG. 6. For E2 and E4, the balance capacitor can be 281 pF minus 8 pF, or 273 pF, implemented as C231 and C232 combined in parallel to achieve the overall desired capacitance value, in FIG. 5 and FIG. 6. The 8 pF capacitance is subtracted to account for the output capacitance of the analog switches U41 and U42. It is noted that the capacitance values provided herein are merely example capacitance values for one particular implementation of an impedance measurement circuit used in AFE 400 of WCD 100, and other capacitance values can be used when other components are used to compensate for the particular capacitance and/or impedance imbalances of those components and circuits, and the scope of the disclosed subject matter is not limited in these respects.

One or more embodiments as described herein can overcome the shortcomings of existing designs by enabling the selection of separate pairs of electrodes for impedance measurements, and in turn, can overcome the resulting input capacitive imbalance by switching in or out additional capacitance on each input line as required.

Figure 7:
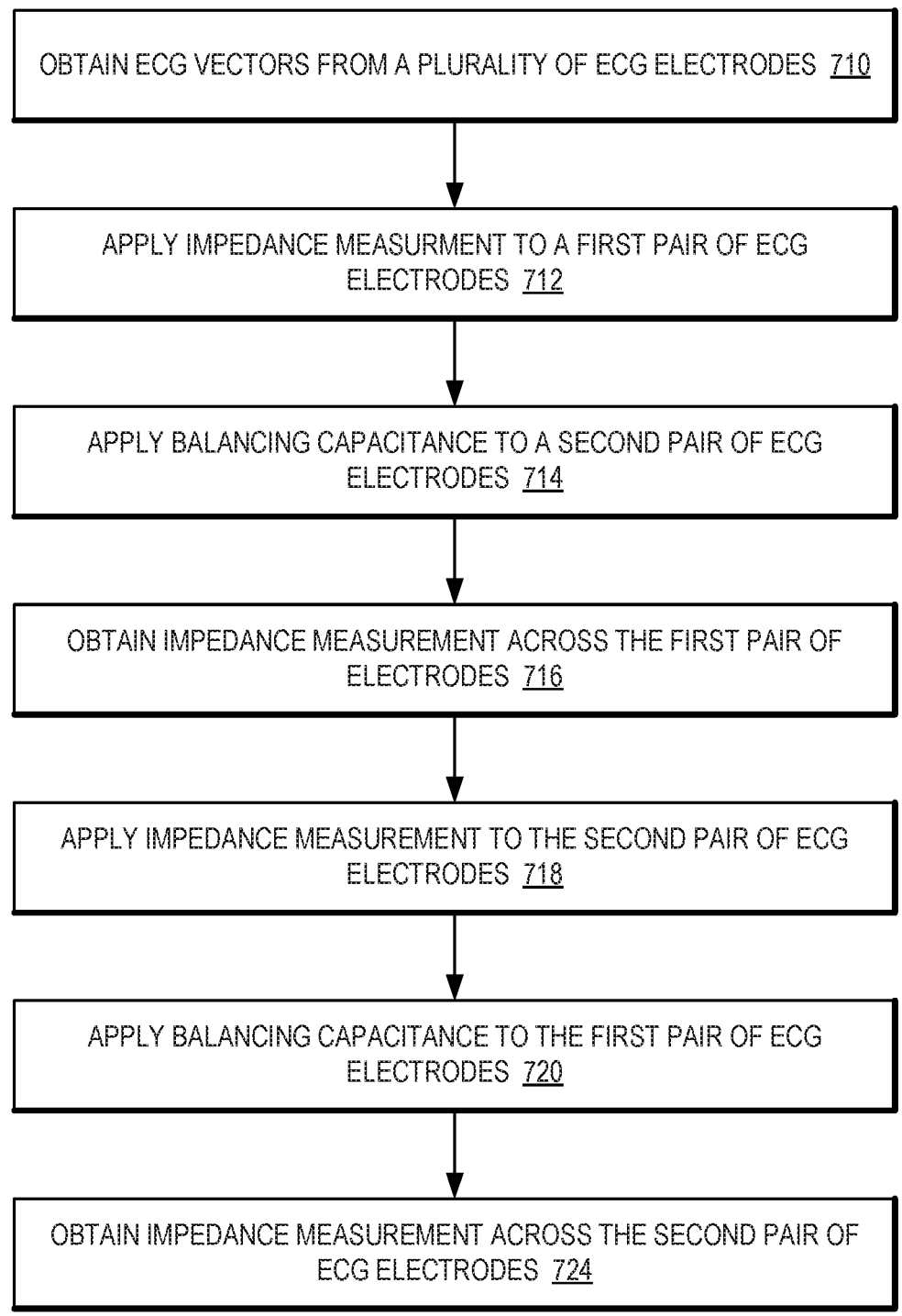
FIG. 7 is a diagram of a method to apply a balancing impedance to a second pair of electrodes when the impedance across a first pair of electrodes is being measured in accordance with one or more embodiments.

Referring now to FIG. 7, a diagram of a method to apply a balancing impedance to a second pair of electrodes when the impedance across a first pair of electrodes is being measured in accordance with one or more embodiments will be discussed. Although method 700 FIG. 7 illustrates one particular order and number of operations, it will be appreciated that other orders or numbers of operations may be provided, and the scope of the disclosed subject matter is not limited in these respects.

At operation 710, an ECG monitor 116 can be used to obtain ECG vectors from a plurality of ECG electrodes. At operation 712, an impedance measurement circuit 500 can be applied across a first pair of the ECG electrodes, and at operation 714 a balancing impedance such as a balancing capacitance can be applied across a second pair or multiple other pairs of ECG electrodes whose impedance is not being measured. At operation 716, an impedance measurement can be obtained across the first pair of the ECG electrodes. It should be noted that the impedance measurement can be made while the ECG monitor 116 is obtaining the ECG vectors from the plurality of ECG electrodes without disturbing or interfering with the process of obtaining the ECG vectors. In some examples, the impedance measurement can also be obtained when the ECG vectors are not being obtained.

At operation 718, the impedance measurement circuit can be switched off the first pair of ECG electrodes and can be applied to the second pair of ECG electrodes. At operation 720 balancing capacitance can be applied to the first pair of ECG electrodes. It should be noted that the balancing capacitance applied to the first pair of ECG electrodes at operation 720 is not necessarily the same value as the balancing capacitance applied to the second pair of ECG electrodes at operation 712. In some examples, the balancing capacitances can have the same or nearly the same values, and in other examples the balancing capacitances can have different values. At operation 724, the impedance measurement across the second pair of electrodes can be obtained which can occur while the ECG vectors are being obtained at operation 710. It should be noted that method 700 may be applied to any N number of ECG electrodes, and method 700 can be expanded to selectively measure a successive pairs of ECG electrodes while applying balancing capacitances to the other pairs of ECG electrodes whose impedances are not being measured, and the scope of the disclosed subject matter is not limited in this respect.

In one or more embodiments, application of method 700 to an ECG monitor 116, either as a standalone ECG monitor or as part of WCD 100, can provide the ability to maintain a high Common Mode Rejection Ration (CMRR) on the ECG inputs of preamp 132 during topology changes which would normally result in a reduced CMRR and thus reduced ECG signal quality. In addition, application of method 700 can allow the monitoring of multiple impedance channels with reduced hardware complexity while still maintaining high ECG signal quality. Such an approach can be used for detecting certain medical conditions such as heart failure or pulmonary edema or effusion. Pulmonary edema refers to fluid collection in the alveoli of the lungs, and pulmonary effusion or pleural effusion refers to water of fluid collecting in layer of the pleura outside the lungs. Using method 700 to monitor multiple impedance channels can enhance the amount of information for both changes in impedance due to breathing and the bulk impedance across the thoracic cavity. Changes in impedance due to respiration can be used to determine the patient's respiration rate which in turn can be tracked over time as a possible indication of heart failure as published in the literature. The bulk impedance measures the total impedance across the thoracic cavity of the patient 110. Using multiple impedance channels for multiple impedance measurements can allow "views" directed to one lung at a time in the "view." This data can then be evaluated to compare the impedance between the lungs or each lung individually over time. In general, liquid such as water in or around the lungs can reduce the impedance of any "view" that included the affected lung as compared to a dry lung. This information, either directly or over time, could then be used to gauge the patient's lung condition.

The following are example implementations of the subject matter described herein. It should be noted that any of the examples and the variations thereof described herein may be used in any permutation or combination of any other one or more examples or variations, although the scope of the claimed subject matter is not limited in these respects.

In example one, a wearable cardioverter defibrillator (WCD) comprises a plurality of electrocardiography (ECG) electrodes, a right-leg drive (RLD) electrode, and a plurality of defibrillator electrodes to contact the patient's skin when the WCD is delivering therapy to the patient, a preamplifier coupled to the ECG electrodes and the RLD electrode to obtain ECG data from the patient as one or more ECG vectors, a high voltage subsystem to provide a defibrillation voltage to the patient through the plurality of defibrillator electrodes, and an impedance measurement circuit to measure an impedance across a first pair of ECG electrodes, wherein the impedance measurement circuit is to apply a balancing impedance across a second pair of ECG electrodes when an impedance of the second pair of ECG electrodes is not being measured. In example two, the plurality of ECG electrodes provides multiple impedance channels to the preamplifier to detect a heart failure of the patient. In example three, the plurality of ECG electrodes provides multiple impedance channels to the preamplifier to detect a pulmonary edema in the patient. In example four, the plurality of ECG electrodes provides multiple impedance channels to the preamplifier to detect a pulmonary effusion in the patient. In example five, the plurality of ECG electrodes provides multiple impedance channels to the preamplifier to detect respiration of the patient. In example six, the impedance measurement circuit includes a switch to select the first pair of ECG electrodes for impedance measurement or the second pair of ECG electrodes for impedance measurement. In example seven, the impedance measurement circuit includes a switch to apply the balancing impedance to the second pair of ECG electrodes when the impedance across the first pair of electrodes is being measured, and to remove the balancing impedance from the second pair of ECG electrodes when the impedance across the first pair of ECG electrodes is not being measured. In example eight, the balancing impedance comprises a capacitance value. In example nine, the impedance measurement circuit is to measure an impedance across the second pair of ECG electrodes, and to apply a balancing impedance across the first pair of the plurality of ECG electrodes when the impedance of the first pair of ECG electrodes is not being measured.

In example ten, a method comprises obtaining a plurality of electrocardiogram (ECG) vectors from a plurality of ECG electrodes, applying an impedance measurement circuit across a first pair of the ECG electrodes, applying a balancing impedance across a second pair of the ECG electrodes, and obtaining an impedance measurement across the first pair of the ECG electrodes while obtaining the plurality of ECG vectors. In example eleven, the method further comprises applying the impedance measurement circuit across the second pair of the ECG electrodes, applying a balancing impedance across the first pair of the ECG electrodes, and obtaining an impedance measurement across the second pair of the ECG electrodes while obtaining the plurality of ECG vectors. In example twelve, the method further comprises using the impedance measurement to detect when the patient is experiencing heart failure. In example thirteen, the method further comprises using the impedance measurement to detect when the patient is experiencing pulmonary edema. In example fourteen, the method further comprises using the impedance measurement to detect when the patient is experiencing pulmonary effusion. In example fifteen, the method further comprises using the impedance measurement to detect respiration of the patient. In example sixteen, said applying a balancing impedance comprises switching a capacitance across the second pair of the ECG electrodes.

In example seventeen, an electrocardiogram (ECG) monitor comprises a plurality of electrocardiography (ECG) electrodes and an electrode to provide a common reference for the plurality of ECG electrodes, a preamplifier coupled to the ECG electrodes and the additional electrode to obtain ECG data from the patient as one or more differential ECG vectors, and an impedance measurement circuit to measure an impedance across a first pair of ECG electrodes, wherein the impedance measurement circuit is to apply a balancing impedance across a second pair of ECG electrodes when an impedance of the second pair of ECG electrodes is not being measured. In example eighteen, the balancing impedance across the second pair of ECG electrodes results in a higher common mode rejection ratio (CMRR) for the preamplifier than when the balancing impedance is not applied when measuring the impedance across the first pair of ECG electrodes. In example nineteen, the impedance circuit is configured to measure impedance across any pair of the ECG electrodes and to apply a balancing impedance across electrodes whose impedance is not being measured. In example twenty, the impedance measurement is used to determine when fluid is in or around a lung of the patient.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment, removing one or more features from an embodiment, or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the operations, acts, or modalities of a method.

Although the claimed subject matter has been described with a certain degree of particularity, it should be recognized that elements thereof may be altered by persons skilled in the art without departing from the spirit and/or scope of claimed subject matter. It is believed that the subject matter pertaining to a wearable cardioverter defibrillator (WCD) with ECG preamp having active input capacitance balancing and many of its attendant utilities will be understood by the foregoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. A wearable cardioverter defibrillator (WCD), comprising:
   a plurality of electrocardiography (ECG) electrodes, a right-leg drive (RLD) electrode, and a plurality of defibrillator electrodes to contact a patient's skin when the WCD is delivering therapy to the patient;
   a preamplifier coupled to the ECG electrodes and the RLD electrode to obtain ECG data from the patient as one or more ECG vectors;
   a high voltage subsystem to provide a defibrillation voltage to the patient through the plurality of defibrillator electrodes; and
   an impedance measurement circuit to measure an impedance across a first pair of ECG electrodes, wherein the impedance measurement circuit is to apply a balancing impedance across a second pair of ECG electrodes when an impedance across the second pair of ECG electrodes is not being measured.

2. The WCD of claim 1, wherein the plurality of ECG electrodes provides multiple impedance channels to the preamplifier to detect a heart failure of the patient.

3. The WCD of claim 1, wherein the plurality of ECG electrodes provides multiple impedance channels to the preamplifier to detect a pulmonary edema in the patient.

4. The WCD of claim 1, wherein the plurality of ECG electrodes provides multiple impedance channels to the preamplifier to detect a pulmonary effusion in the patient.

5. The WCD of claim 1, wherein the plurality of ECG electrodes provides multiple impedance channels to the preamplifier to detect respiration of the patient.

6. The WCD of claim 1, wherein the impedance measurement circuit includes a switch to select the first pair of ECG electrodes for impedance measurement or the second pair of ECG electrodes for impedance measurement.

7. The WCD of claim 1, wherein the impedance measurement circuit includes a switch to apply the balancing impedance to the second pair of ECG electrodes when the impedance across the first pair of ECG electrodes is being measured, and to remove the balancing impedance from the second pair of ECG electrodes when the impedance across the first pair of ECG electrodes is not being measured.

8. The WCD of claim 1, wherein the balancing impedance comprises a capacitance value.

9. The WCD of claim 1, wherein the impedance measurement circuit is to measure an impedance across the second pair of ECG electrodes, and to apply a balancing impedance across the first pair of the plurality of ECG electrodes when the impedance of the first pair of ECG electrodes is not being measured.

10. The WCD of claim 1, wherein the first pair of ECG electrodes is selected for impedance measurement when an ECG signal detected with the first pair of ECG electrodes has less noise than an ECG signal detected with the second pair of ECG electrodes, and the second pair of ECG electrodes is selected for impedance measurement when the ECG signal detected with the second pair of ECG electrodes has less noise than the ECG signal detected with the first pair of ECG electrodes.

11. An electrocardiogram (ECG) monitor, comprising:
    a plurality of electrocardiography (ECG) electrodes and an additional electrode to provide a common reference for the plurality of ECG electrodes;
    a preamplifier coupled to the ECG electrodes and the additional electrode to obtain ECG data from a patient as one or more differential ECG vectors; and
    an impedance measurement circuit to measure an impedance across a first pair of ECG electrodes, wherein the impedance measurement circuit is to apply a balancing impedance across a second pair of ECG electrodes when an impedance across the second pair of ECG electrodes is not being measured.

12. The ECG monitor of claim 11, wherein the balancing impedance across the second pair of ECG electrodes results in a higher common mode rejection ratio (CMRR) for the preamplifier than when the balancing impedance is not applied when measuring the impedance across the first pair of ECG electrodes.

13. The ECG monitor of claim 11, wherein the impedance measurement circuit is configured to measure impedance across any pair of the ECG electrodes and to apply a balancing impedance across electrodes whose impedance is not being measured.

14. The ECG monitor of claim 11, wherein the impedance measurement is used to determine when fluid is in or around a lung of the patient.

15. The ECG monitor of claim 11, wherein a pair of the ECG electrodes is selected for impedance measurement when an ECG signal detected with the pair of ECG electrodes is less noisy than ECG signals detected with other sets of ECG electrodes.

\* \* \* \* \*